(12) United States Patent
Minekawa et al.

(10) Patent No.: US 9,401,015 B2
(45) Date of Patent: Jul. 26, 2016

(54) DEFECT CLASSIFICATION METHOD, AND DEFECT CLASSIFICATION SYSTEM

(75) Inventors: Yohei Minekawa, Tokyo (JP); Yuji Takagi, Tokyo (JP); Minoru Harada, Tokyo (JP); Takehiro Hirai, Tokyo (JP); Ryo Nakagaki, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 360 days.

(21) Appl. No.: 14/112,105

(22) PCT Filed: Apr. 16, 2012

(86) PCT No.: PCT/JP2012/002609
§ 371 (c)(1),
(2), (4) Date: Nov. 25, 2013

(87) PCT Pub. No.: WO2012/144183
PCT Pub. Date: Oct. 26, 2012

(65) Prior Publication Data
US 2014/0072204 A1     Mar. 13, 2014

(30) Foreign Application Priority Data

Apr. 20, 2011  (JP) ................................. 2011-093603

(51) Int. Cl.
*G06K 9/00*     (2006.01)
*G06T 7/00*     (2006.01)
(Continued)

(52) U.S. Cl.
CPC .............. *G06T 7/001* (2013.01); *G01N 23/225* (2013.01); *G06K 9/6267* (2013.01); *G06T 5/00* (2013.01); *G01N 21/9501* (2013.01); *G01N 2223/421* (2013.01); *G01N 2223/611* (2013.01);
(Continued)

(58) Field of Classification Search
CPC .... G01N 23/225; G06K 9/6267; G06T 7/001; G06T 5/00; G06T 7/0006
See application file for complete search history.

(56) References Cited

U.S. PATENT DOCUMENTS 6,246,787 B1 *  6/2001  Hennessey ....... G01N 21/95607
                                           250/559.45
6,906,794 B2 *  6/2005  Tsuji .................. G01N 21/9503
                                           356/237.4
(Continued)

FOREIGN PATENT DOCUMENTS

JP       08-021803 A     1/1996
JP       11-282822 A    10/1999
(Continued)

*Primary Examiner* — Gregory M Desire
(74) *Attorney, Agent, or Firm* — Mattingly & Malur, PC

(57) ABSTRACT

In automatic defect classification, a classification recipe must be set for each defect observation device. If a plurality of devices operate at the same stage, the classification class in the classification recipes must be the same. Problems have arisen whereby differences occur in the classification class in different devices when a new classification recipe is created. This defect classification system has a classification recipe storage unit; an information specification unit, the stage of a stored image, and device information. A corresponding defect specification unit specifies images of the same type of defect from images obtained from different image pickup devices at the same stage. An image conversion unit converts the images obtained from the different image pickup devices at the same stage into comparable similar images; and a recipe update unit records the classification classes in the classification recipes corresponding to the specified images of the same type of defect.

14 Claims, 18 Drawing Sheets

(51) Int. Cl.
  *G01N 23/225* (2006.01)
  *G06K 9/62* (2006.01)
  *G06T 5/00* (2006.01)
  G01N 21/95 (2006.01)
  H01L 21/66 (2006.01)

(52) U.S. Cl.
  CPC . *G01N2223/646* (2013.01); *G06T 2207/10061* (2013.01); *G06T 2207/30148* (2013.01); *H01L 22/12* (2013.01); *H01L 22/20* (2013.01); *H01L 2924/0002* (2013.01)

(56) References Cited

U.S. PATENT DOCUMENTS

| | | | |
|---|---|---|---|
| 7,991,217 | B2 | 8/2011 | Nakagaki et al. |
| 8,175,373 | B2 * | 5/2012 | Abbott ................ G06T 7/0006 356/237.4 |
| 2003/0130806 | A1 * | 7/2003 | Mizuno ............. G01R 31/2894 702/35 |
| 2003/0202178 | A1 * | 10/2003 | Tsuji ................ G01N 21/9503 356/237.2 |
| 2004/0218806 | A1 | 11/2004 | Miyamoto et al. |
| 2005/0075841 | A1 * | 4/2005 | Peles ..................... G06T 7/0004 702/185 |
| 2008/0167829 | A1 * | 7/2008 | Park .................... G01N 21/8851 702/81 |
| 2009/0136117 | A1 * | 5/2009 | Barkol .................. G01N 21/93 382/145 |
| 2009/0196489 | A1 * | 8/2009 | Le ....................... G01N 21/9503 382/148 |
| 2010/0310150 | A1 * | 12/2010 | Hayashi ................ G06K 9/469 382/145 |
| 2011/0101223 | A1 * | 5/2011 | Fukuda ................ H01J 37/244 250/310 |
| 2014/0072204 | A1 * | 3/2014 | Minekawa ........... G01N 23/225 382/149 |

FOREIGN PATENT DOCUMENTS

| | | |
|---|---|---|
| JP | 2000-057349 A | 2/2000 |
| JP | 2004-047939 A | 2/2004 |
| JP | 2004-226328 A | 8/2004 |
| JP | 2005-274285 A | 10/2005 |
| JP | 2007-225531 A | 9/2007 |
| WO | 2012/046431 A1 | 4/2012 |

* cited by examiner (a)

(b)

FIG.7
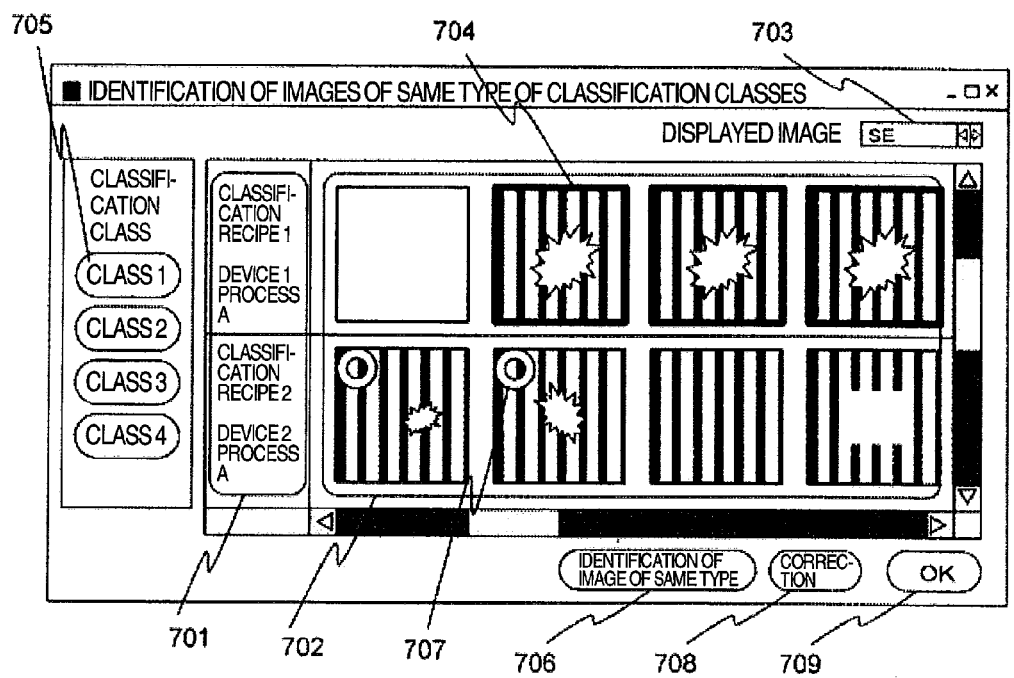
FIG.8
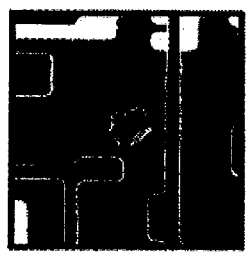
(a) UPPER IMAGE
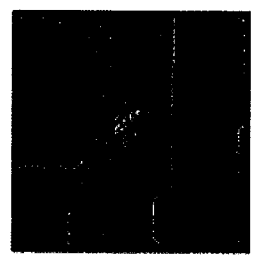
(b) LEFT IMAGE
(c) RIGHT IMAGE (a)　　　　　　　　　　　　　(b)

(a)          (b)

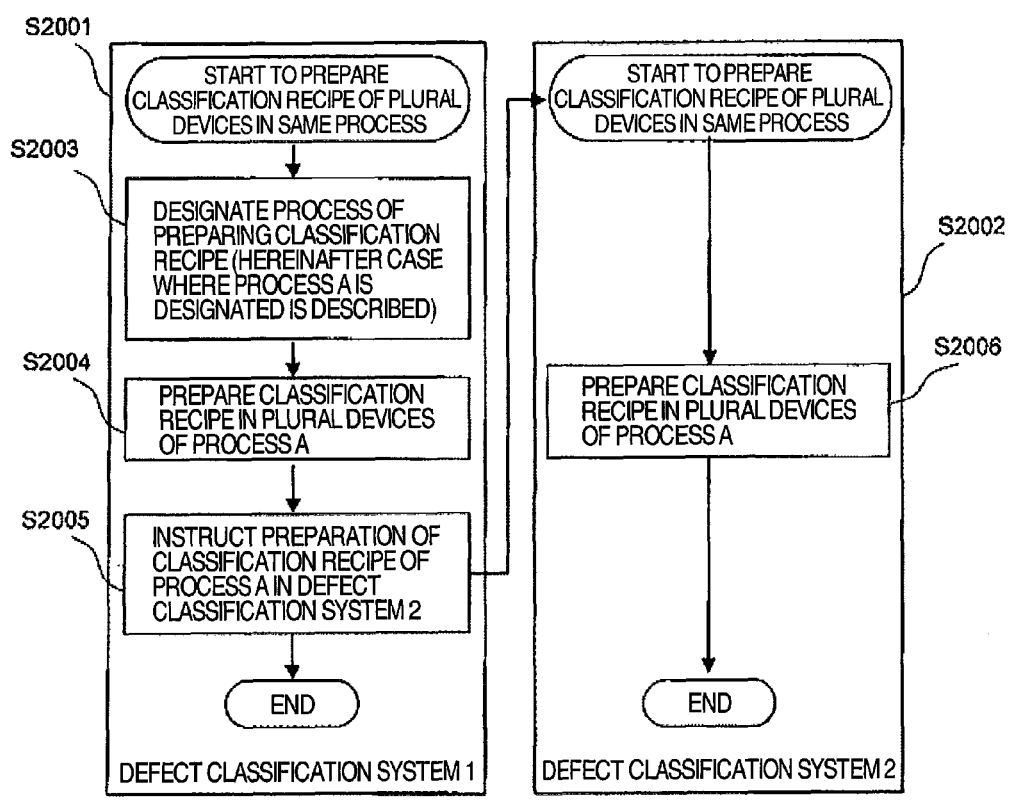

DEFECT CLASSIFICATION METHOD, AND DEFECT CLASSIFICATION SYSTEM

TECHNICAL FIELD

The present invention relates to a defect classification method and a defect classification system for classifying defects and the like on a semiconductor wafer.

BACKGROUND ART

In a fabrication process of semiconductors, it is important to clear up the cause of occurrence of a defect on a semiconductor wafer in order to improve the yield. In the existing circumstances, a defect inspection device and a defect observation device are used to analyze a defect in the semiconductor fabrication field.

The defect inspection device employs optical means or an electron beam to observe a wafer and produces positional coordinates of a detected defect. Since it is important for the defect inspection device to make processing over the wide range at high speed, the data amount of image to be obtained is reduced by increasing the pixel size of the image (that is, low resolution) as large as possible. In many cases, even if existence of a defect can be confirmed from the detected image of low resolution, it is difficult to identify a kind of the defect (defect type) in detail.

Accordingly, the defect observation device is used for identification of the defect type. The defect observation device employs output information of the defect inspection device to photograph defect coordinates of wafer with high resolution and produce an image or picture. Miniaturization of the fabrication process of semiconductor devices is advanced, so that the size of defect also reaches the several nm range with the miniaturization and the resolution of several nm range is required in order to observe the defect in detail.

Therefore, in recent years, the defect observation device (review SEM) using a scanning electron microscope (SEM) is employed widely. The review SEM has the function of automatic defect review (ADR) for automatically collecting high-resolution images of defects (defect images) on a wafer by using the defect coordinates produced by the defect inspection device.

In recent years, the throughput of ADR of the review SEM is improved and accordingly it is desired that operation of identifying the defect type from a large amount of defect images collected is automatized. The review SEM has the function of automatic defect classification (ADC) for automatically identifying the defect type from the defect images to be classified.

As a method of automatically classifying the defect images for each defect type, Patent Literature 1 describes a method of processing the defect images to quantify the feature amount of external appearance of the defect part and classify defects using a neural network, for example. Further, as a method of being capable of easily coping with even the case where there are many kinds of defects (defect types) to be classified, Patent Literature 2 describes a method of classifying the defects by combining a rule base classification method with an instruction classification method, for example.

In the automatic classification of defect images, classification is performed on the basis of classification recipes. The classification recipes contain various parameters such as image processing parameters, information of the defect types to be classified (classification classes), defect images belonging to the classification classes (instruction pictures) and the like. When a new defect type is produced due to variation in the fabrication process, a classification class of the new defect is added in the classification recipes to be updated. Patent Literature 3 describes a method in which when the defect images are automatically classified, a new defect is judged as a defect of which the classification class is not clear (unknown defect) and a new classification class is added to the classification recipes to be updated. Further, the unknown defect contains a defect which occurs due to instruction error by the user and exists beyond the classification class defined in the classification recipes.

Heretofore, there are circumstances in which classification of defect images is manually performed by a person before the defect observation device and accordingly the defect observation device generally has the automatic classification function of defect images as part of the function thereof. However, with increase of production quantities of semiconductor products, a plurality of defect observation devices are introduced in the fabrication line of semiconductor wafers and there arises a problem that a cost for management of the classification recipes is increased. As opposed to this problem, Patent Literature 4 describes a method in which a plurality of image detection devices are connected to an information processing device through a network and photographed images are transferred to the image processing device so that the image processing device judges whether anything unusual appears in the images or not.

CITATION LIST

Patent Literature

PATENT LITERATURE 1: JP-H-8-21803
PATENT LITERATURE 2: JP-A-2007-225531
PATENT LITERATURE 3: JP-A-2000-57349
PATENT LITERATURE 4: JP-A-2004-226328

SUMMARY OF INVENTION

Technical Problem

The above-mentioned ADC function is the function of calculating various features containing size, shape and the like of defect part from the photographed SEM images as feature amounts and classifying defects into plural defect classes defined in advance on the basis of the calculated feature amounts. At present, the review SEM's are put on the market by some makers and the makers mount the ADC function on the defect classification system (defect classification device) which is sold in combination with the review SEM of the respective makers to be provided. The defect classification system has not only the above-mentioned automatic classification function of defect images but also the display function for showing the classification result thereof to the user, the function of receiving input from the user to correct the automatic classification result or the function of transferring the classification result to a data base server installed in the fabrication line to manage the yield.

A plurality of observation devices of different types are frequently used in the management operation of the yield in the semiconductor device fabrication. As a reason thereof, for example, improvement of reliability of observation operation and improvement of the operation rate of device are enumerated. The plural defect observation devices are used to photograph images, so that the data amount can be increased and the reliability and the operation rate of device can be improved. Further, there is also a case where purchase timing of device and reception timing of device from the device maker are not coincident so that the plural devices of different types must be used. Further, the devices of different types contain devices of plural different makers and devices of different types of the same maker.

When the types of devices are different, performance and characteristics thereof are different in many cases and accordingly it is demanded for management work of yield to employ plural devices having such different performance and characteristics efficiently. This demand is applied even to the review SEM and the defect classification system accompanying them. That is, the demand for the defect classification system which classifies images of plural review SEM's having different types is increased.

Usually, the fabrication of semiconductor wafers includes plural processes and since defect types occurring due to difference in process are different, classification recipes are generally prepared in accordance with processes. Further, when a device of different maker or type is applied to a wafer in the same process, parameters suitable for classification are often different since performance and characteristics of the device are different. Moreover, even if a maker or a type of device is the same, the quality of image photographed is different due to difference in performance between devices (instrumental error). Accordingly, it is necessary to prepare classification recipes for each combination of the defect observation device and process.

Here, it is supposed that plural defect observation devices are connected through a network as described in the Patent Literature 4 so as to observe a defect on a wafer in the same process. FIG. 1 schematically illustrates a conventional system configuration example in which image photographing devices 101, 101' are connected to corresponding classification modules 103, 103', which are connected to corresponding classification recipes 104, 104', respectively. Further, the classification modules 103, 103' are connected to a yield management database server 105 through communication means 106 such as a network. In the classification procedure, images obtained from plural image photographing devices (in FIG. 1, two devices of image photographing devices 1 and 2) are subjected to defect classification by the classification modules 103, 103' corresponding to the respective devices. The classification modules 103, 103' perform classification on the basis of the classification recipes 104, 104' and the classification results thereof are transmitted to the yield management database server 105 through the communication means 106 to be stored. Here, the image photographing devices 101, 101' correspond to the above defect observation devices and the classification modules 103, 103' represent devices which can perform ADC.

When the image processing devices 1 and 2 photograph a wafer in the same process, it is preferable that defect images obtained by the respective devices are classified into the same classification class. Therefore, the classification classes of the classification recipes 1 and 2 must be the same and the photographed images having defect of the same type (hereinafter referred to as defect image of same type) must be registered in each classification class. Hereinafter, when the classification classes of plural classification recipes are the same and defect images registered in all classification classes are of the same type in the same classification class, it is supposed that the classification definition is the same. Further, the same classification class means that the defect type desired to be classified in the classification class is the same and when the defect type desired to be classified is the same, the defect type is referred to as the same classification class even if the name or the like of the classification class is different.

The conventional system configuration example has a problem that there is a possibility that the classification definition is not maintained to be the same in each of the classification recipes 104 when the classification recipes are set individually since the classification recipes themselves exist in each of image photographing devices separately. For example, in the case of FIG. 1, as described in the explanation of the Patent Literature 3, the case where a new defect occurs and the classification recipe 104 of the classification module 103 corresponding to one image photographing device 101 is updated is taken into consideration. In this case, the classification recipe 104' of the classification module 103' corresponding to the other image photographing device 101' is not updated since the classification recipe 104' is independent of the classification recipe 104 and as a result there is a possibility that there is difference in the classification definition in each of the classification recipes in the same manner as the case where the classification classes are set individually as described above.

As described above, in the Patent Literatures 3 and 4, the above problem arising when the defect observation devices of plural makers or different types are operated in the same process is not recognized and any method of maintaining the classification definition to be the same so as to solve the problem is not described.

Accordingly, the present invention is to solve the above problem and to provide a defect classification system and a defect classification method of maintaining classification definition to be the same to improve reliability of statistical process management even if a plurality of different defect observation devices are operated in the same process.

Solution to Problem

Summary of representatives of the inventions disclosed in this patent specification is briefly described as follows:

(1) A defect classification method of classifying defect images using classification recipes corresponding to a device which photographs a sample and a process in which the sample is manufactured, comprises a step of defining the same classification class as a classification class defined by a classification recipe of a first image photographing device by a classification recipe of a second image photographing device corresponding to the same process as the classification recipe of the first image photographing device, a step of specifying a defect image of the same type as an instruction image registered in the classification class defined by the classification recipe of the first image photographing device from among defect images photographed by the second image photographing device, and a step of registering the specified defect image in the same classification class as the classification class of the first image photographing device in which the instruction image is registered, among classification classes defined by the classification recipe of the second image photographing device.

(2) A defect classification system connected to plural image photographing devices through communication means, comprises classification means to classify defect images photographed by the plural image photographing devices and classification recipe management means to manage classification recipes in which information for classification is stored, and the classification recipe management means includes a corresponding defect specifying part to specify a defect image of the same type as an instruction image registered in a classification class of a classification recipe in a first image photographing device which is one of the plural image photographing devices from among defect images photographed by a second image photographing device which is one of the plural image photographing devices installed in same process and an image conversion part to convert the instruction image to resemble the defect image obtained from the second image photographing device.

Advantageous Effects of Invention

According to the present invention, there can be provided the defect classification method and the defect classification system which solve the above problems and improve the reliability of statistical process management by maintaining the classification definition in plural classification recipes corresponding to the same process to be the same.

BRIEF DESCRIPTION OF DRAWINGS

FIG. 7 is a diagram illustrating an example of GUI for specifying defect images of the same type in the defect classification system of the embodiment 1;

FIG. 8 shows examples of images obtained by the image photographing device of the embodiment 1;

FIG. 20 is a flow chart showing classification recipe preparation processing of the defect classification system of the embodiment 3.

DESCRIPTION OF EMBODIMENTS

Figure 1:
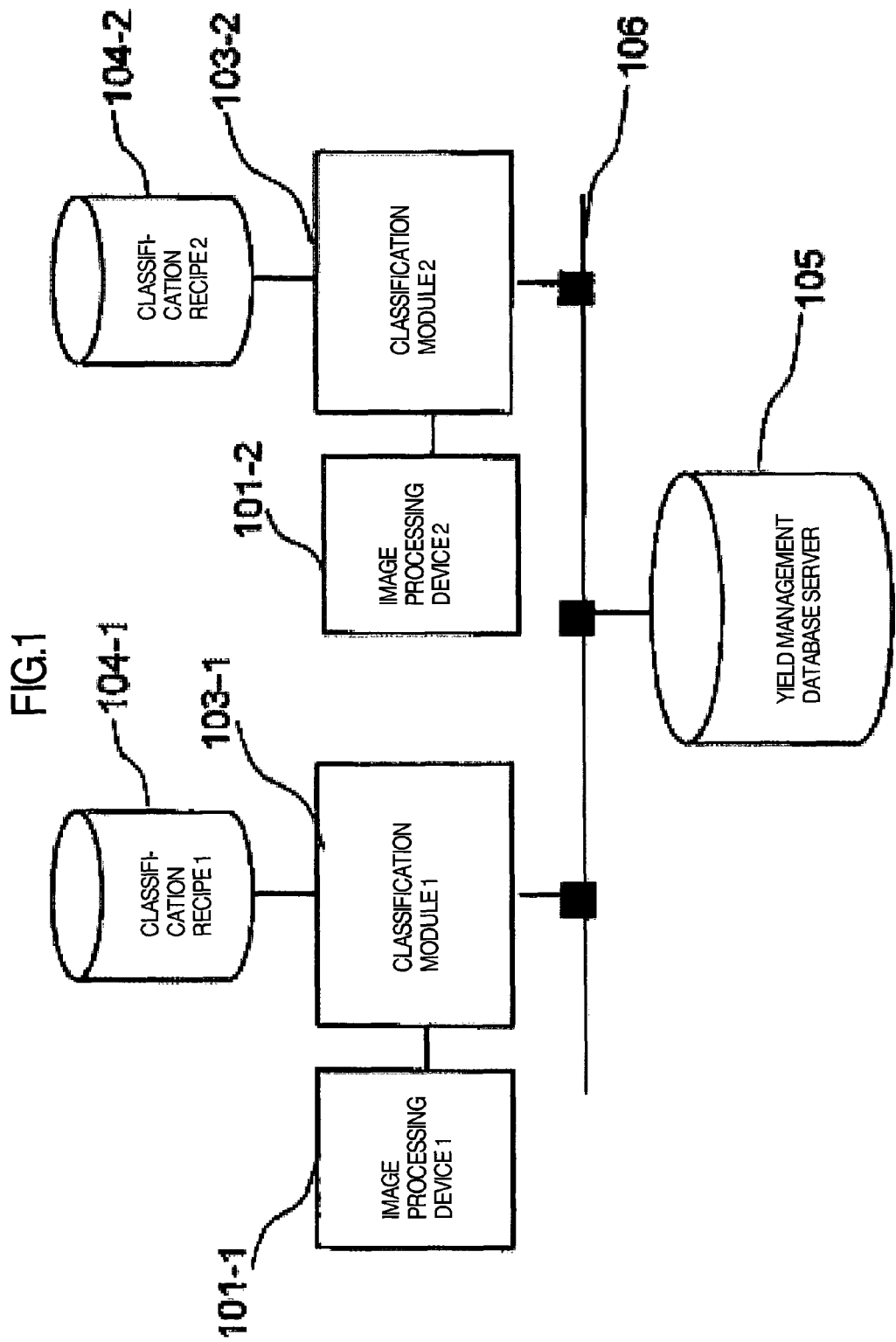
FIG. 1 is a diagram schematically illustrating a system configuration example of image photographing devices and classification modules in a conventional defect classification system.

Embodiments of the present invention are now described with reference to the drawings in detail. Like elements are given like reference numerals as a rule throughout all drawings for explaining the embodiments and repeated description thereof is omitted. Further, in the embodiments, description is made to the case where defect images photographed by an image photographing device provided with SEM are classified, although a defect classification system according to the present invention may be supplied with any images except SEM image or may be supplied with defect images photographed using optical means, ion microscope or the like except SEM image.

Embodiment 1

A first embodiment of a defect classification system according to the present invention is described with reference to FIG. 2. A defect classification system 201 of the first embodiment is connected with N (N≥2) image photographing devices 200-1~200-$n$ through communication means 204 such as a network. The image photographing devices 200 (200-1~200-$n$) are devices which take images of relevant part and its detailed configuration is described later.

The defect classification system 201 has the function of receiving defect images obtained by the plural image photographing devices and classifying them to be outputted as classification results to an input/output part 217 structured using keyboard, mouse and display devices and the like to display data to an operator and receive input from the operator. The defect classification system 201 of the first embodiment is described below in detail.

The defect classification system 201 includes a recipe management part 202 which executes preparation and update processing of classification recipes and stores therein classification recipes, defect images and information accompanying the defect images, a classification module 203 which classifies the defect images inputted from the image photographing devices, a whole control part 205 which controls operation of the devices and an input/output I/F part 206 which performs data transfer of defect images and the like through the input/output part 217 or the communication part 204.

The recipe management part 202 includes a processing part 207 which executes processing relative to the classification recipes and a storage part 208 which stores therein information. The storage part 208 includes an image memory part 213 which stores therein defect images photographed by the image photographing devices 200, a classification recipe memory part 214 which stores therein classification recipes prepared for each of the image photographing devices 200 or processes and an accompanying information memory part 215 which stores therein accompanying information such as processes obtained from the image photographing devices together with defect images for each of defect images. Further, the processing part 207 includes a corresponding defect specifying part 209 which specifies the defect image of the same type for defect images obtained from the image photographing devices 200, an information specifying part 210 which specifies information of a process and an apparatus photographed for each of classification recipes and defect images, a recipe update part 211 which performs preparation of the classification recipes and update of the classification classes, and an image conversion part 212 which converts images by image processing. Further, the information specifying part 210 specifies the classification recipe in the same process on the basis of process information for each of defect images stored in the classification recipe specifying part 214 and the accompanying information memory part 215 and specifies process information of defect images and information of photographed devices stored in the image memory part 213. The procedure and the method of processing of the processing part 207 are described later.

The classification module 103 includes a classification processing part 216 which classifies defect images on the basis of the classification recipes. Detailed processing of the classification processing part 216 is described later.

Further, an example of the defect classification system 201 shown in FIG. 2 may be operated in a single arithmetic and logic unit (hereinafter abbreviated to PC) or may be operated in plural PC's in a division manner. When the defect classification system is operated in the plural PC's, a method in which the recipe management part 202 is operated as a recipe server in a single PC, for example, is also considered. Furthermore, in the example of the defect classification system 201 shown in FIG. 2, an example where one classification module 203 is provided is shown, although plural classification modules may be used to configure the defect classification system. When the plural classification modules are provided, the method in which each of classification modules is operated in different PC and the classification module which processes defect images photographed in each of the image photographing apparatuses is assigned to each PC is also considered. The modification example shown here can be applied to even the embodiments described later.

Figure 3:
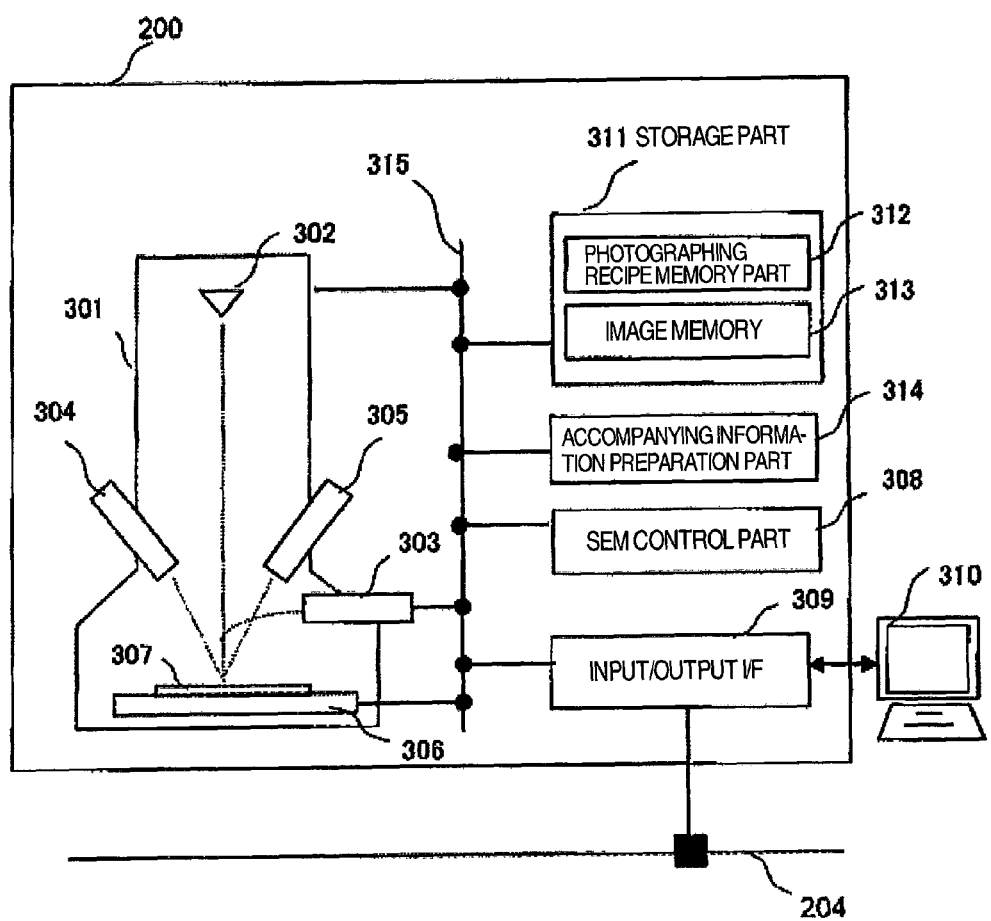
FIG. 3 is a diagram schematically illustrating a configuration example of an image photographing device of the embodiment 1.

FIG. 3 is a diagram schematically illustrating a detailed configuration example of the image photographing device 200. The image photographing device 200 includes an SEM column 301, an SEM control part 308, an input/output I/F 309, a storage part 311 and an accompanying information preparation part 314, which are connected to one another through communication means 315. The input/output I/F 309 is connected to an input/output part 310, which performs input/output of data to the operator.

The SEM column 301 includes an electron source 302, a stage 306 on which a sample wafer 307 is put and plural detectors 303, 304 and 305 which detect secondary electrons and backward scattered electrons generated from the sample wafer 307 as a result of irradiation of primary electron beam on the sample wafer 307 from the electron source 302. Further, although not shown, the SEM column 301 includes deflectors for scanning the primary electron beam on an observation area of the sample wafer 307, an image production part for converting the strength of the detected electrons into digital signal to produce a digital image and the like in addition.

The storage part 311 includes a photographing recipe memory part 312 in which acceleration voltage, probe current, frame addition number (the number of images used in processing of reducing influence of shot noise by obtaining plural images in the same place and preparing an average image thereof), visual field size and the like are stored and an image memory 313 which stores therein obtained image data.

The accompanying information production part 314 has the function of preparing information accompanying each image data, for example, photographing conditions such as acceleration voltage, probe current and frame addition number upon photographing, ID information for specifying a photographing device, kinds and property of detectors 303 to 305 used to produce images, ID and process of wafer and accompanying information such as date and time that images are photographed. Information of ID and process of wafer may be inputted by the user from the input/output part 310 or may be read in from the surface of the wafer or may be read out from a box (not shown) in which wafers are housed. The prepared accompanying information is transferred together with image data when the image data is transferred through the input/output I/F 309.

The SEM control part 308 controls all processing performed by the image photographing device 200 such as obtainment of images. Movement of the stage 306 for moving a predetermined observation portion on the sample wafer 307 into the visual field of photographing, irradiation of primary electron beam on the sample wafer 307, detection of electrons generated from the sample wafer 307 by the detectors 303 to 305, imaging of detected electrons and storage of images in an image memory 313, preparation of accompanying information to the photographed images by the accompanying information preparation part 314 and the like are performed in response to instructions from the SEM control part 308. Various instructions and designation of photographing conditions from the operator are performed through the input/output part 310 including keyboard, mouse, display and the like.

Further, the configuration of the image photographing device 200 shown in FIG. 3 is an example and when a maker or a type is different, the configuration and the number of detectors 303 to 305 are sometimes different. When the maker or the type is different, differences that the photographed image itself obtained and the image quality of the photographed image are different due to difference in configuration and property of the detectors occur even if the same defect is photographed. Because of the differences, it is difficult to compare the defect images obtained by different devices in the state that defects are photographed as they are. As described above as the problem, in order to make the classification definition of the classification recipes in the image photographing devices identical, it is necessary to compare the defect images photographed by different image photographing devices with one another and specify the defect images of the same type. In the present invention, the differences in the photographed images are absorbed and the defect images of the same type can be specified from among the defect images obtained by different devices. The differences in the photographed images and the method of capable of absorbing the differences to make comparison are described with reference to FIGS. 8 to 11 later.

Figure 4:
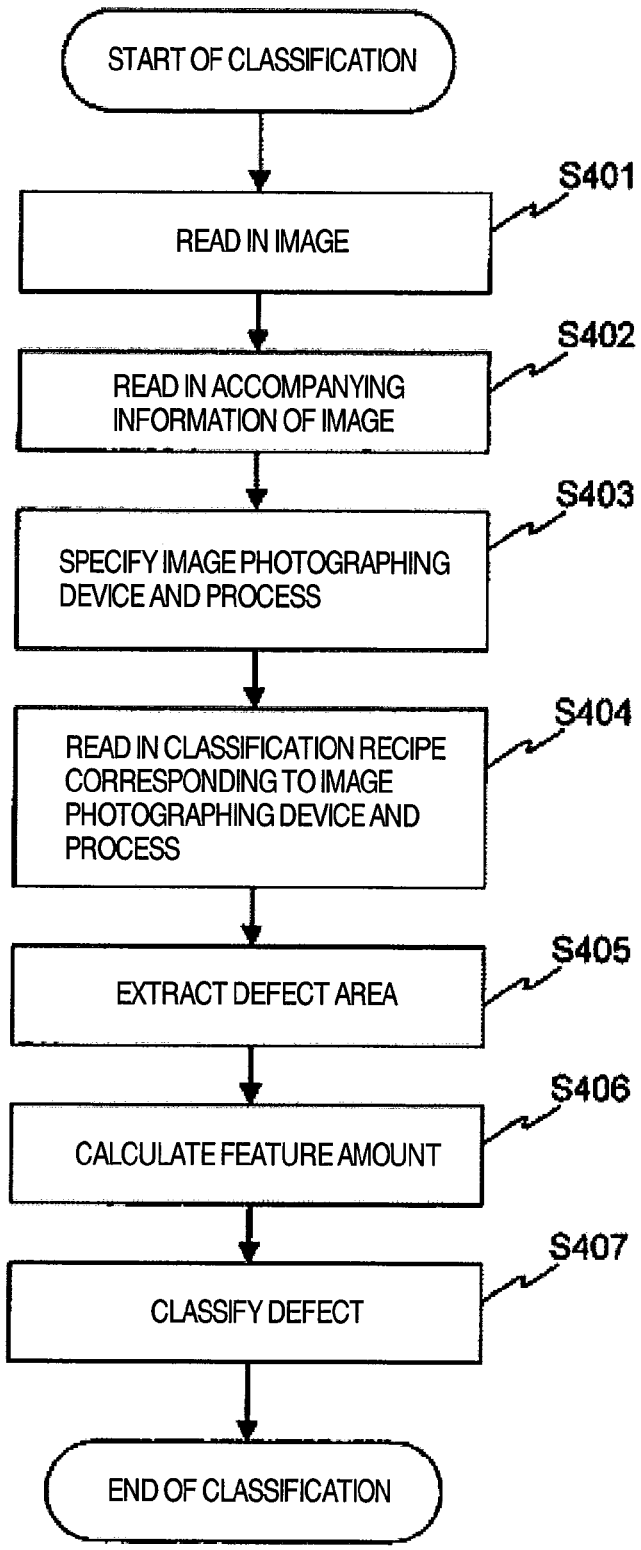
FIG. 4 is a flow chart showing the classification processing of the defect classification system of the embodiment 1.

Referring now to FIG. 4, the processing flow of classifying inputted defect images in the defect classification system according to the present invention is described. The processing of classifying the defect images is performed by the classification processing part 216 of the classification module 203.

First, a defect image to be classified is read in from the image memory part 213 (S401). Next, accompanying information of the defect image is read in from the accompanying information memory part 215 (S402). Here, the accompanying information is conditions at the time of image photographing and at least contains ID for identifying the image photographing device which photographs the defect image and ID for identifying a process of a photographed wafer. Further, acceleration voltage and probe current in photographing, visual field size of photographing, photographing date and time, photographing coordinates and the like may be stored and used as information at the time of classification. Next, the information specifying part 210 specifies the image photographing device which photographed the defect image and a process of photographed wafer (S403). In the specifying of processing S403, ID's of the image photographing device and the process contained in the accompanying information of the defect image read out in processing S402 may be used. Alternatively, hierarchy structure (directory structure) may be formed in the image memory part 213 and the defect image transmitted from the image photographing device may be divided into hierarchy (directory) in each of image photographing devices and processes in which the defect image was photographed to be stored, so that the image photographing device and the process may be specified. Next, a classification recipe corresponding to the image photographing device and the process in which the defect image to be classified was photographed among classification recipes provided for image photographing devices and processes is read in from the classification recipe memory part 214 (S404). The production method of the classification recipes is described later with reference to FIG. 5. Further, the classification recipes described here include information of classification classes in the classification processing, instruction pictures belonging to the classification classes, classification parameters containing information of classification identification aspect for classifying defect images into classification classes and parameters of processing of extracting defect area from the defect image and processing of calculating the feature amount. Next, a defect area is extracted from the read-in defect image (S405). Then, a value (feature amount) obtained by quantifying the feature concerning the defect in the extracted defect area is calculated (S406). Finally, the calculated feature amount and the classification identification aspect contained in the classification recipe are used to classify the image (S407). As the classification method of defect, the neural network, the support vector machine (SVM) or the like may be used or the rule type classification device and the instruction type classification device may be used in combination as described in the Patent Literature 2. The foregoing has described the processing flow in case where the defect image of one defect inputted is classified, although in order to classify plural defect images, the processing of S401 to S407 may be repeatedly performed by the number of the defect images.

Figure 5:
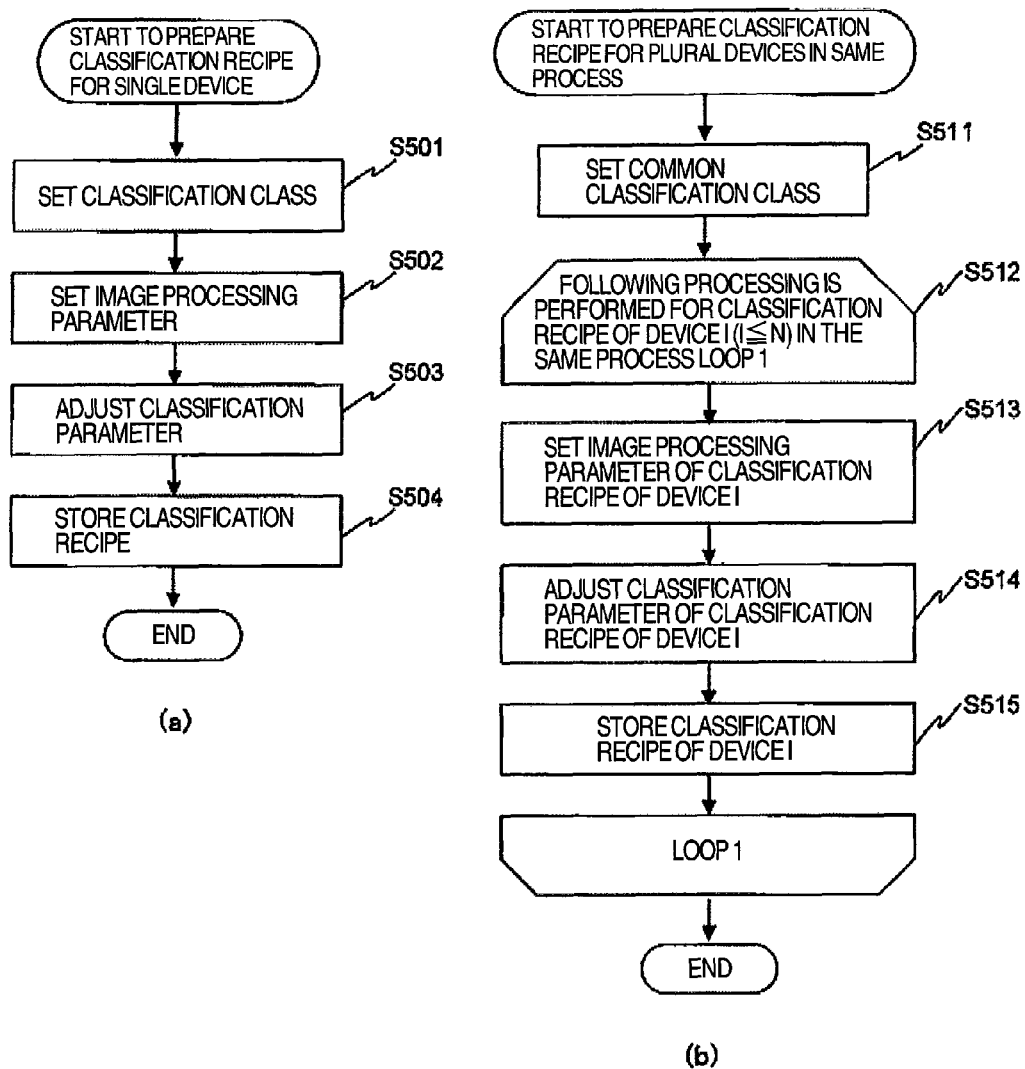
FIG. 5 is a flow chart showing the classification recipe preparation processing of the defect classification system of the embodiment 1.

Referring now to FIG. 5, the method of preparing the classification recipes is described in detail. The classification recipes is information that defines the classification method of defect images and includes classification classes (defect type) of defects, image processing parameter and classification parameter containing information of the classification identification aspect for classifying defects into classification classes and the like. As described above, the classification recipes are required to be prepared for each of image photographing devices and processes and on the premise that the classification recipes are prepared, it is necessary that the defect image photographed in combination of device and process in which the classification recipe is desired to be prepared is stored in the image memory part 213.

FIG. 5(*a*) shows a conventional classification recipe preparation (classification recipe preparation for single device) method of preparing classification recipes one by one for each device and process and FIG. 5(*b*) shows the classification recipe preparation method according to the present invention.

First, referring to FIG. 5(*a*), the classification recipe preparation method for single device which is a conventional method is described. The definition of the classification classes and instruction pictures are registered to thereby set the classification classes (S501). Here, the classification classes are defined and instruction pictures are registered in respective classification classes. Next, image processing parameters in the image processing for recognizing defect area and wiring pattern in a defect image are set (S502) and classification parameters are adjusted (S503). The classification recipes prepared in this manner are stored in the classification recipe memory part (S504). In the setting processing S502 of the image processing parameters, the image processing parameters are set so that image processing result proper for the instruction image registered in processing S501 is obtained. For example, adjustment of the classification parameters in the processing S503 may be performed by the method of instructing the instruction picture registered in processing S501 to the classification processing part in the classification module and preparing the classification identification aspect and when the instruction picture exists in each classification class, the adjustment can be made automatically.

Next, referring to FIG. 5(*b*), the classification recipe preparation method according to the present invention is described. The processing of FIG. 5(*b*) is processed by the recipe update part 211. In the preparation method (FIG. 5(*b*)) of the classification recipes according to the present invention, the classification recipes of plural image photographing devices in the same process can be prepared in a lump and additionally the classification definition about all classification recipes prepared can be made identical. First, common classification class for the classification recipes of the plural image photographing devices is set (S511). Here, the classification class common to all classification recipes is defined and the defect image of the same type is registered in each classification class as the instruction image. Detailed description of the processing S511 in the present invention is made later with reference to FIGS. 6 and 7. Next, in processing S512, the following processing of S513 to S515 is performed for the classification recipe corresponding to N image photographing devices (N≥2) in the same process which perform the common classification class setting in processing S511. The image photographing device in the same process corresponding the classification recipe which performs the common classification class setting in processing S511 is defined as a device i (1≤i≤N). Then, the image processing parameter of the classification recipe of the device i is set (S513) and the classification parameter of the classification recipe of the device i is adjusted (S514). The prepared classification recipe of the device i is stored in the classification recipe memory part 214 (S515). The object to be processed in processing of S513 to S515 is classification recipe of the device i and the processing may be performed by the same method as the processing of S502 to S504.

Setting of the image processing parameter in the processing of S502 and S513 may be read in from a previously defined table or may be defined by the user manually. In the embodiment, when the image processing parameter is read in from the previously defined table, the classification recipes of N devices in the same process can be prepared by performing only the processing S511 by the user.

Further, in the processing S513, the user may set the image processing parameters for only the first device 1 (i=1) manually and an image processing parameter conversion table described later may be used to convert the image processing parameters set for the device 1 into the image processing parameters for other devices to be used. Here, the image processing parameter conversion table is a table in which values corresponding to the image conversion processing parameters and calculation expressions for conversion are defined for each combination of devices i desired to be converted from the image processing parameters of the device (here, device 1) for the image processing parameter conversion. When the image processing parameter conversion table is used, the user can prepares the classification recipes of N devices in the same process only by performing the processing S511 and the processing S513 for the device 1.

Figure 6:
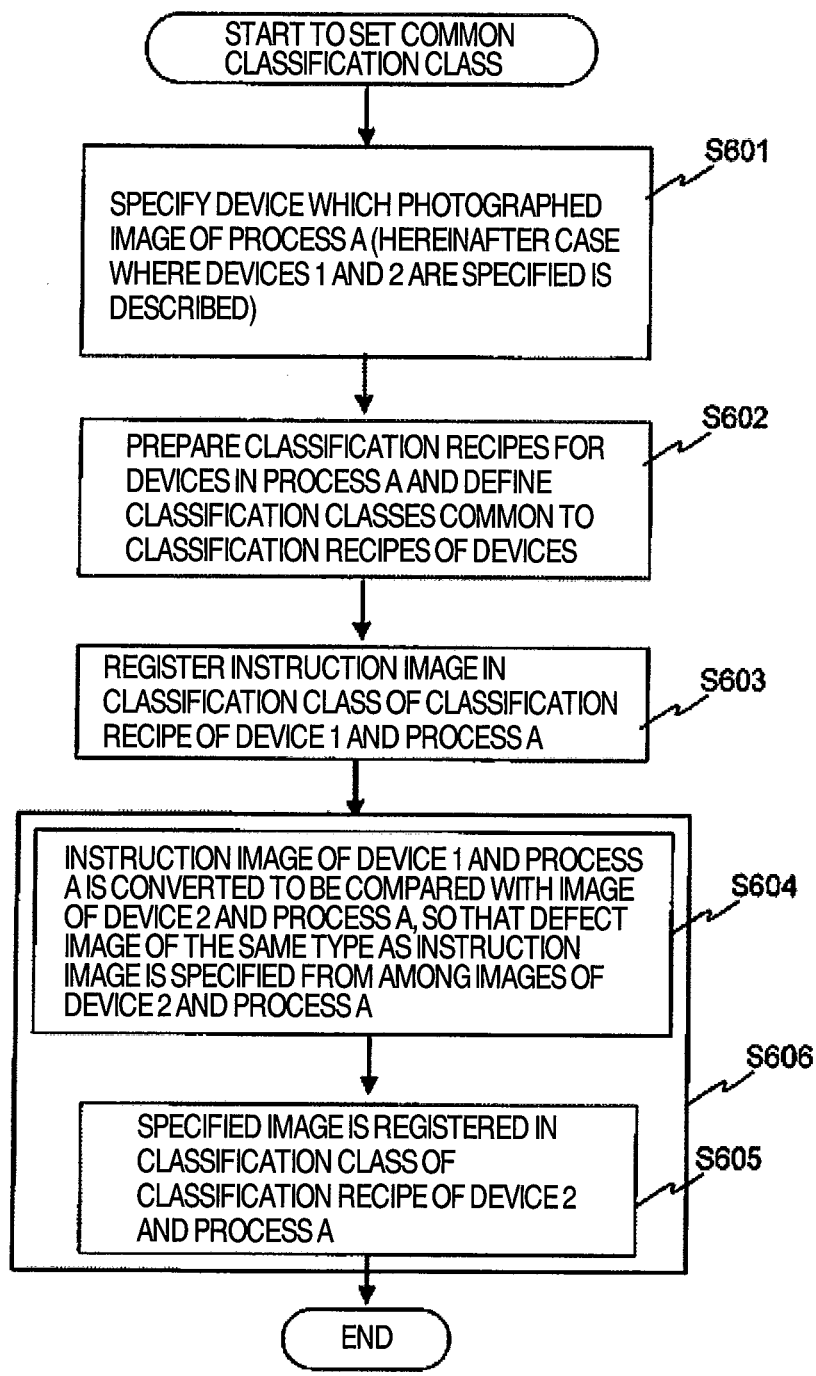
FIG. 6 is a flow chart showing the classification class setting processing of the defect classification system of the embodiment 1.

FIG. 6 is a flow chart showing an example of processing flow at the time of setting common classification class in the classification recipe preparation in the defect classification system according to the present invention and shows detailed processing of S511 of FIG. 5. The processing flow shown in FIG. 6 can define the common classification classes in plural classification recipes corresponding to plural image photographing devices of the same process and register the defect images of the same type in the classification classes as instruction images, so that the classification definition can be made identical in all classification recipes. Further, in description of the processing flow using the drawings in this patent specification including FIG. 6, the image photographing device is abbreviated as a device and the process of photographed wafer is abbreviated as a process. Further, the classification recipe for classifying the defect image photographed in the process A of the device 1 is abbreviated as the classification recipe of device 1 and process A and the defect image photographed from the process A of the device 1 is abbreviated as the defect image of device 1 and process A (or image of device 1 and process A). Even if the devices and the processes are different like device 2 and process B, description thereof is made in the same abbreviation manner.

In FIG. 6, the case where the classification recipe of the process A is prepared is described in case where there are two devices (devices 1 and 2). On the premise that the classification class is set, the defect image photographed in combination of the process (process A) and the device (device 1, 2) desired to set the classification class is required to be stored in the image memory part 213.

First, the device which photographed a defect image in a process A stored in the image memory part 213 is specified by the information specifying part 210 (S601). As the specifying method of the device which photographed the defect image of the process A, the device may be judged from accompanying information or the like for each defect image stored in the accompanying information memory part 215 or the like or may be designated by the user from the input/output part 217.

Next, classification recipes for devices (devices 1 and 2) in the process A are prepared and classification classes common to the devices are defined (S602). At this time, the classification class of the classification recipe of device 1 and process A and the classification recipe of device 2 and process A can be defined identically. Part or all of the defect images of device 1 and process A stored in the image memory part 213 are registered in the classification class of the classification recipe of device 1 and process A as instruction image (S603). Registration of the classification class and instruction image in processing of S602 and S603 may be made by the user's designation using input/output part 217 or may be made on the basis of information of the classification class defined in a file and the defect image to be registered read out therefrom. Next, in processing S606, the defect image of device 2 and process A stored in the image memory part 213 is registered for the classification classes of the classification recipe of device 2 and process A. In the processing S606, first, the image (defect image of the same type) in which the defect is photographed and has the same type as the defect image registered as the instruction image in the classification class of the classification recipe of device 1 and process A in the processing S603 among the defect images of device 2 and process A is specified by the corresponding defect specifying part 209 (S604). As the specifying method of the defect image of the same type, the defect image registered as the instruction image in the classification classes of device 1 and process A is converted into the image photographed by the device 2 and the feature amounts of their images are compared with each other to thereby specify the defect image of the same type as the instruction image from among the defect images of device 2 and process A. By specifying the defect image of the same type, the user may register the instruction image in only the classification recipe of device 1 and process A and registration of the instruction image to the classification recipe of device 2 and process A can be performed automatically. Further detailed description of this specifying method is described later with reference to FIG. 12. Finally, the defect image of device 2 and process A specified in the processing S604 is registered in the classification class corresponding to the classification recipe of device 2 and process A (S605). In FIG. 6, the case where there are provided two devices 1 and 2 has been described as an example, although even if three or more devices are provided, the processing S606 is performed repeatedly by the number of devices, so that this processing flow is applicable.

FIG. 7 shows an example of GUI for performing processing of S603 to S605 upon setting of the classification class described in FIG. 6 in the defect classification system according to the present invention. Even in FIG. 7, description is made by taking the case where the classification recipe of process A is prepared for two devices (devices 1 and 2) similarly to the description of FIG. 6 as an example.

In FIG. 7, 701 represents information of names of devices and processes in which defect image in process A was photographed and 702 represents plural defect images photographed in devices and arranged in display areas corresponding to the devices. 703 represents a combo box for selecting a defect image to be displayed and, for example, secondary electron image or backward scattered electron image photographed by the detectors 303 to 305 can be selected. 704 represents defect images selected as defects of the same type by the user for defects of device 1 and process A and the defect image can be judged by highlighting frames or image. The mouse, keyboard or pen tablet of the input/output part 217 may be used to select the image or information such as defect ID for specifying the image may be described in a file and read out to select the image. 705 represents a button for registering the image selected in device 1 and process A in the classification class defined in processing S602 (S603). The method of registering the image in the classification class is not limited to the form that a button on a picture is depressed and there is considered a method of registering the image by a drag-and-drop operation using a mouse after selection. 706 represents a button for specifying the defect image of the same type as the defect image registered as the instruction image in the classification class in device 1 and process A from the image of device 2 and process A (S604). 707 represents a mark indicating the defect image of the same type specified in the processing S604. The image may be enclosed by frame or the image may be highlighted to be discriminated from other images. Further, the name or mark of the classification class may be shown in the image. The defect image of the same type may be specified for each classification class or in lump for plural classification classes. 708 represents a button for correcting or changing the defect image to be registered in the classification class of device 2 and process A when the user judges that the defect image of device 2 and process A specified in processing S604 is not the same type as the defect image registered as an instruction image in device 1 and process A. 709 represents a button for registering the defect image of device 2 and process A specified in processing S604 in the classification class corresponding to the classification recipe of device 2 and process A. Further, when the defect image specified by the button 708 is changed, the changed defect image is registered in the classification class corresponding to the classification recipe of device 2 and process A.

In processing S604, in order to make comparison of the defect image obtained from a device of a different maker or type to specify the defect image of the same type, difference of the photographed image itself or difference in quality of the photographed image caused by difference in configuration or property of detector may be considered. The following description is made with reference to FIGS. 8 to 11.

The image photographing device 200 shown in FIG. 3 includes 3 detectors and can take three images at observation place on the sample wafer at the same time. FIG. 8 shows examples of three photographed images taken about foreign matter on the surface of the sample wafer. FIG. 8(a) shows an image taken by detecting secondary electrons generated from the sample wafer by the detector 303. FIGS. 8(b) and (c) show images taken by detecting backward scattered electrons generated from the sample wafer by two detectors 304 and 305. The image shown in FIG. 8(a) is named upper image and the images shown in FIGS. 8(b) and (c) are named left and right images, respectively. In the upper image of FIG. 8(a), circuit pattern and outline of a defect part are observed clearly. On the other hand, in the left and right images of FIGS. 8(b) and (c), shade produced due to uneven states of the surface can be observed. Such difference in property of the images is produced by arrangement of the detectors, the energy band of detected electrons provided in the detectors, electromagnetic field given in the column influencing orbit of generated electrons from the sample and the like. Further, the quality of image is varied by photographing conditions such as, for example, acceleration voltage of electrons, probe current and frame addition number.

Figure 9:
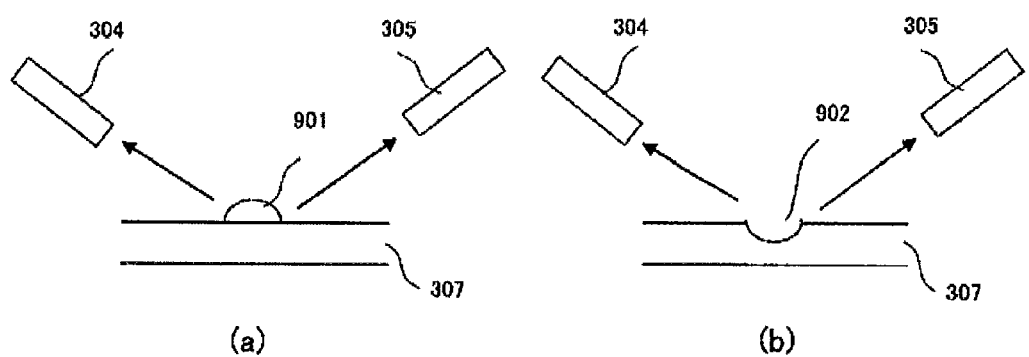
FIG. 9 illustrates an example of the sections of defects and arrangement of detectors in the image photographing device of the embodiment 1.
Figure 10:
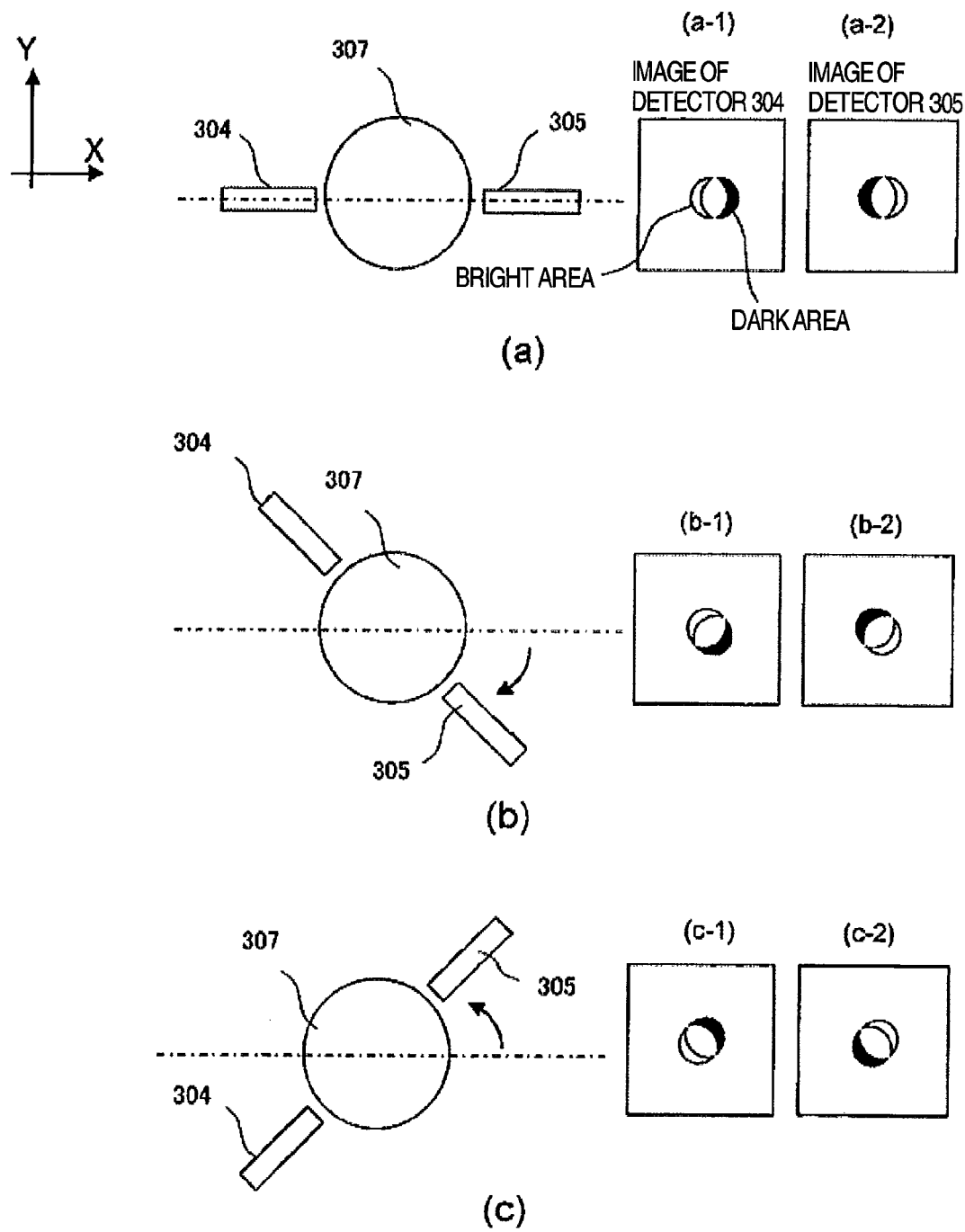
FIG. 10 illustrates arrangement of detectors and directions of detected shades in the image photographing device of the embodiment 1.
Figure 11:
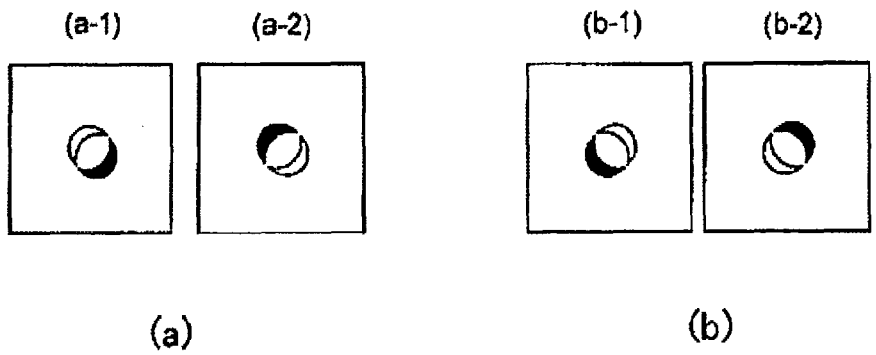
FIG. 11 shows examples of shade detection images in the image photographing device of the embodiment 1.

The relation of direction of the detectors 304 and 305 for backward scattered electrons and the shade of the images is described as an example where the properties of obtained images are different due to difference in the characteristics of the detector with reference to FIGS. 9 to 11. FIG. 9 schematically illustrates the positional relation between sections of the sample wafer 307 and the detectors 304 and 305 for backward scattered electrons in case where projecting defect 901 and hollow defect 902 exist on the sample wafer 307. As shown in FIG. 9, the two detectors for backward scattered electrons are disposed in opposite position at obliquely upper position of the sample wafer 307. Primary electron beam comes from just above. Since the backward scattered electrons generated from an observation part has the characteristics that its energy is strong and directivity is provided, the backward scattered electrons generated in the direction toward one detector almost never reach the detector disposed in the opposite side. As a result, as shown in FIGS. 8(b) and (c), the images in which shade formed according to the uneven state of the observation part can be observed can be obtained.

Further, the direction of the shade is changed when the relative position of the detectors 304 and 305 to the sample wafer 307 is changed. FIG. 10 schematically illustrates the direction of the detectors and the direction of the shade of the images taken. FIG. 10(a) illustrates an example in which the detectors are disposed along the X direction of the coordinate system. Images (a-1) and (a-2) schematically illustrate the images obtained by the detectors 304 and 305, respectively. In FIG. 10(a), shades of bright and dark areas on the images (a-1) and (a-2) obtained from the detectors 304 and 305 appear in the X direction. Here, the bright area is an area where brightness is high on the image. The bright area means that a lot of backward scattered electrons generated from the part are detected by the detector and the dark area means that the backward scattered electrons generated from the part is not detected by the detector. Since the backward scattered electrons have the directivity, the bright and dark areas on the image are decided depending on the generation direction of the backward scattered electrons in each part and position and direction of the detectors which detect the backward scattered electrons so that the bright and dark areas appear. FIG. 10(b) shows the case where the detectors are rotated by 45 degrees clockwise as compared with FIG. 10(a). The direction of shades on images (b-1) and (b-2) obtained by the detectors disposed as shown in FIG. 10(b) is rotated in a corresponding manner to rotation of the detectors. Similarly, FIG. 10(c) shows the case where the detectors are disposed in the position rotated by 45 degrees counterclockwise as compared with FIG. 10(a). Similarly, the direction of shades on images (c-1) and (c-2) obtained by the detectors disposed as shown in FIG. 10(c) is rotated in a corresponding manner to rotation of the detectors. In this manner, when the direction of the detectors is changed, the direction of shades is changed.

On the other hand, it is necessary to take care that the direction of shades is changed even by uneven states of the object. That is, it is necessary to take care that the direction of shades is opposite in projecting defect and hollow defect shown in FIGS. 9(a) and 9(b). Accordingly, for example, as shown in FIGS. 11 (a) and (b), when images can be obtained by the detectors 304 and 305, it cannot be judged whether an object to be observed is projecting or hollow if there is no information about configuration of the detectors. Actually, in this example, FIG. 11(a) shows an image of a projecting defect obtained by the configuration of the detectors shown in FIG. 10(b) and FIG. 11(b) shows an image of a hollow defect obtained by the configuration of the detectors shown in FIG. 10(c). In this manner, when the images detected by the detectors having different configuration are compared, it is understood that there is a fear that the relation of projection and hollow of the defect part is recognized wrongly.

Figure 2:
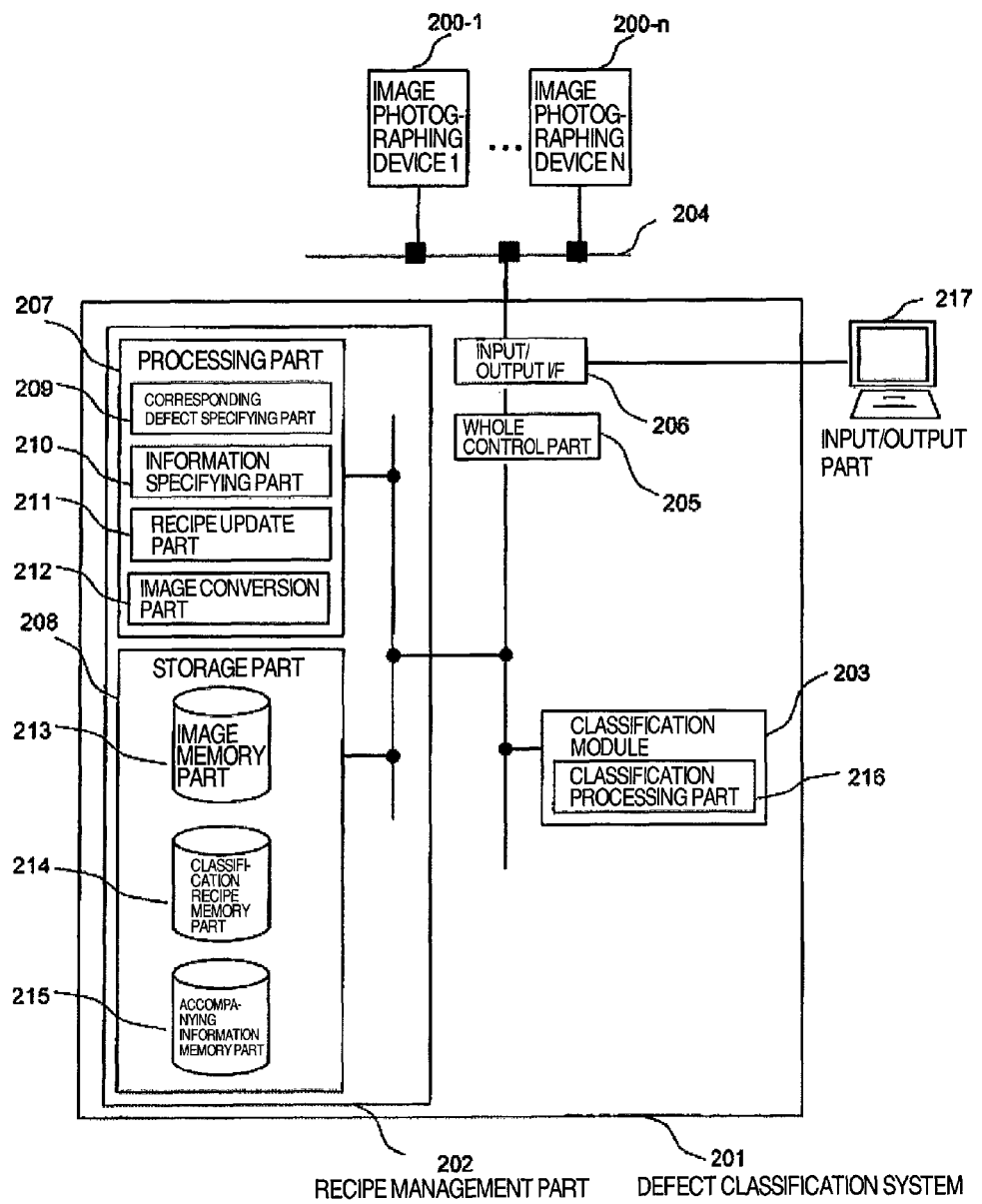
FIG. 2 schematically illustrates a configuration example of a defect classification system of an embodiment 1.

In the defect classification system of the embodiment shown in FIG. 2, the plural image photographing devices 200 are connected, although there is a case where the types of the image photographing devices are different. For example, there is a case where makers which provide the devices are different or even if the maker is the same, there is a case where plural products or devices having different configuration of detectors are provided. In the description made so far, the number of detectors in the image photographing device is three and description has been made by taking the case where relative position to the sample is changed when detectors for detecting backward scattered electrons are opposite as an example, although there is considered the case where the number of detectors, the direction of detectors, energy band to be detected and even other conditions are different for each device. Moreover, since generated energy of the sample is changed even under conditions at the time of photographing, there is a possibility that even images obtained are changed under the conditions.

As described above, images obtained by devices of different makers or types cannot be compared with each other as they are due to difference in photographed images themselves caused by difference in configuration or characteristics of detectors and difference in image quality of photographed images and it is difficult to specify the defect image of the same type. Accordingly, in the present invention, the images to be compared are subjected to image conversion by the image conversion part 212 to solve difference in the photographed images themselves caused by difference in configuration or characteristics of the detectors and difference in image quality of the photographed images, so that the images to be compared are converted into comparable images.

The image conversion processing performed by the image conversion part 212 is described. The image conversion processing means a series of processing in which an image set is inputted and corresponding accompanying information is read out from the accompanying information memory part 215, so that the accompanying information is processed to output the image set. Concretely, the image conversion processing contains image quality improvement processing, conversion processing in shade direction, mixture processing of images and the like.

As the improvement processing of image quality, there is noise reduction processing, for example. In SEM, when probe current is low at the time of image photographing or when the frame addition number is small, the image having reduced S/N is apt to be obtained. Further, even under the same photographing conditions, when the device to be photographed is different, the image having different S/N is sometimes obtained due to different electron detection rate of the detector. Even in the case of the device of the same type, if the degree of adjustment is different, there is also a possibility that difference in S/N caused by instrumental error between devices occurs. As a concrete example of noise reduction processing, there is processing using various noise filters. An example of the processing method is now described by taking the case where an image similar to an image photographed by a device 2 which can photograph an image with high S/N is prepared or produced from an image photographed by a device 1 which can photograph an image with low S/N as an example. First, the image photographed by the device 1 is subjected to noise filter processing. A sample of the image photographed by the device 2 is prepared and dispersion values of brightness values in flat parts in the image of the device 2 and the image subjected to the noise filter processing of the device 1 are compared, so that the above processing is repeated until a near value (for example, a value at the time that difference in dispersion of the brightness values exceeds a predetermined value) is reached. The above processing is an example but the image similar to the image of the device 2 can be prepared from the image of the device 1 by the above processing.

As another example of the image quality improvement processing, there is sharpness conversion processing for reducing difference in sharpness due to fuzz of the image caused by a beam diameter of the primary electron beam. In SEM, a part to be observed is scanned by a focused electron beam having a diameter of several nanometer range but this beam diameter influences the sharpness of the image. That is, when the beam is thick, an image is fuzzy and the image having reduced sharpness is obtained. In other words, in plural devices having different focusing performance of primary electron beam, an image having different sharpness is obtained. In order to obtain an image having higher sharpness from the obtained image, deconvolution processing is effective and conversely in order to obtain an image having lower sharpness from the obtained image, a low-pass filter is effective. An example of the processing method is now described by taking the case where an image similar to an image photographed by a device 2 which can photograph an image with high sharpness is prepared or produced from an image photographed by a device 1 which can photograph an image with low sharpness as an example. First, an image of the device 1 is subjected to deconvolution processing. A sample of an image of the device 2 is provided and the image of the device 1 subjected to the deconvolution processing and the image of the device 2 are subjected to fourier transform processing or the like to calculate the intensity of frequency. The above processing is repeated until the intensity of high-frequency component reaches the same degree (for example, until difference in the intensity of high-frequency components of both images exceeds a predetermined threshold value). The above processing is an example but the processing can prepare the image similar to the image obtained by the device 2 from the image of the device 1.

Further, as another example of the image quality improvement processing, there is contrast conversion processing. This processing contains processing of removing change in brightness when the brightness of image is changed slowly over the whole surface of visual field of observation by electrification phenomenon on the surface of a sample and processing of correcting the brightness of a circuit pattern part and defect part to obtain an image having high visibility. In SEM, the relation of light and darkness is sometimes reversed in the circuit pattern part and the non-pattern part when photographing conditions are different or when type of photographing device is different even under the same photographing conditions. The contrast conversion processing can correct the brightness reversed as above to unify the external appearance of the image photographed under different conditions or between different devices. An example of the processing method is described by taking the case where an image similar to an image photographed by a device 2 which can photograph an image with high contrast is prepared or produced from an image photographed by a device 1 which can photograph an image with low contrast as an example. First, the image of the device 1 is subjected to the contrast conversion processing. A sample of the image of the device 2 is prepared and the above processing is repeated until an average of the brightness and dispersion of the image of the device 1 subjected to the contrast conversion processing and the image of the device 2 reach the same degree (for example, until difference between the average of the brightness and dispersion of both images exceeds a predetermined threshold value). The above processing is an example but the processing can prepare the image similar to the device 2 from the image of the device 1.

As another example of the image conversion processing, there is conversion processing of shade information. For example, as shown in FIG. 10, information of the shade obtained by detecting the backward scattered electrons is influenced by the arrangement form of detectors in the device strongly. As exemplified in FIG. 11, when images having different arrangement form of detectors are mixed, there is a possibility that judgment of uneven state is mistaken and accordingly in order to prevent it, images having converted direction of shade are prepared.

Concretely, in order to convert the shade direction, the geometric conversion processing such as rotation processing for image and mirror image inversion processing is performed. However, the whole image is subjected to the rotation processing and the inversion processing and accordingly it is necessary to take care that only the shade direction cannot be changed. Accordingly, when the rotation and inversion processing is performed, the circuit pattern and the like photographed are also converted similarly. However, this is not a problem in the processing that the shade is analyzed to judge unevenness. The reason is that usually the defect image and a reference image are compared with each other to judge the unevenness, although if both the images are subjected to the same rotation and inversion processing, pattern information is removed when comparison is made and only shade of part (that is, defect part) where there is a difference between the defect image and the reference image can be extracted.

Furthermore, as an example of another image conversion processing, there is mixing processing of images. FIG. 8 shows an example where the secondary electrons and the backward scattered electrons are separately detected to obtain three images by three detectors of the image photographing device shown in FIG. 3, although when the type of device is different, it is supposed that the number of detectors and the kind of detected electrons are different. Accordingly, the plural detected images are mixed to prepare plural different images. For example, when a device 1 can obtain completely separated images of the secondary electron image and the backward scattered image and on the other hand another device 2 can detect the image in which both the images are mixed, plural images in which images are mixed can be produced from the completely separated and detected images of the device 1 to thereby prepare the image similar to the image obtained by the device 2. The above-exemplified image conversion processing procedures of various types are performed not only singly but also it is a matter of course that the processing procedures are combined to be performed.

Further, there is considered a method in which when the image conversion for preparing an image similar to an image photographed by a device 2 from an image photographed by a device 1 is performed, a parameter table for conversion is previously prepared to perform conversion processing using parameters in the table. Here, the parameter table for conversion is a table in which processing contents of image conversion processing, processing procedures, parameters used in each processing and the like are described in each combination of devices (device 2) desired to prepare similar images from devices (device 1) which photographed original images.

Figure 12:
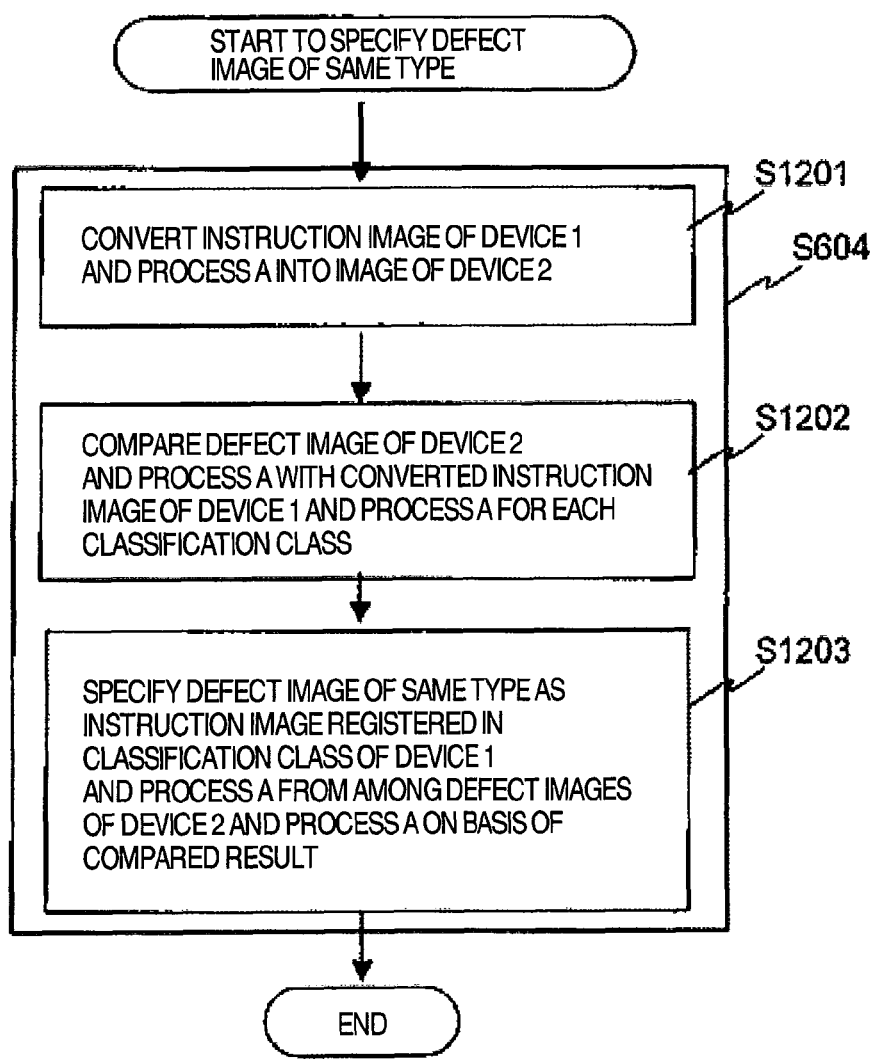
FIG. 12 is a flow chart showing processing for specifying defect image of the same type of the defect classification system of the embodiment 1.

Next, an example of the processing flow of specifying the defect image of the same type as the instruction image in processing S604 in the defect classification system according to the present invention is described in detail with reference to FIG. 12. In FIG. 12, description is made by taking the case where in the case of two devices (devices 1 and 2), an instruction image is already registered in device 1 and process A and a defect image of the same type as the instruction image is specified from among images of device 2 and process A which are defect images photographed from the same process by the device 2 as an example. It is premised that defect images of device 2 and process A are stored in the image memory part 213.

First, the instruction image registered in the classification class in the device 1 and process A is converted into an image similar to the image photographed by the device 2 by means of the image conversion part 212 (S1201). Next, in processing S1201, the defect image of device 2 and process A stored in the image memory part 213 is compared with the converted instruction image of device 1 and process A for each classification class (S1202). The defect image of the same type as the instruction image registered in the classification class of device 1 and process A is specified for each classification class from among the defect images of device 2 and process A on the basis of the compared result (S1203). As a method of specifying the defect image of the same type in processing S1203, a method in which the feature amount such as uneven degree and size of the defect part is calculated from the image and when the feature amount is close, the image is judged as the defect image of the same type may be used. Further, a method of judging the defect image of the same type by using the classification processing part 216 is also considered. In this case, the image converted in each classification class is instructed to the classification processing part 216 and the defect image of the same type as the converted image among the images of device 2 and process A is classified into the classification class. When the defect image of the same type is specified, there is a case where parameters for specification are required in calculation of the feature amount, the specification processing or the like, although specific parameters may be previously defined in a file or may be designated by the user before processing of FIG. 12. Further, in processing S1201, instead of converting the instruction image of device 1 and process A into the image of device 2, the defect image of device 2 and process A may be converted into the image of device 1 to be compared with the instruction image of device 1 and process A. Additionally, the instruction image of device 1 and process A and the defect image of device 2 and process A may be converted into images photographed by a device 3 different from devices 1 and 2 and the converted images may be compared with each other in processing S1202. The device 3 may be a device installed in the same process or if the device 3 can made conversion of images, the device 3 may be a device installed in a different process.

When the defect image of the same type is specified in processing S604, the case where defect image of the same type is not stored in the image memory part 213 and cannot be specified in processing 1203 or the case where the number of the specified defect images of the same type is small and it is insufficient for instruction of the classification processing part 216 is also considered. In this case, in processing S605, part or all of images converted in processing S1201 may be registered in the classification class of the classification recipe of device 2 and process A.

When the devices 1 and 2 are of the same maker and the same type and difference in photographed images is as small as instrumental error between the devices, the processing of S1202 and S1203 is not performed and part or all of the images obtained by converting the instruction image of the device 1 may be registered in the classification class of the classification recipe of device 2 and process A. Further, when the instrumental error between the devices 1 and 2 is sufficiently small, the image conversion in processing S604 is not performed and part or all of the instruction image of device 1 may be registered in the classification class of the classification recipe of device 2 and process A.

Further, in FIG. 12, description has been made by taking the case where two devices 1 and 2 are provided as an example, although even if there are three or more devices, it is needless to say that the processing S604 is performed correspondingly to the number of devices, so that the processing flow can be applied.

When the classification recipes for the plural devices in the same process are prepared by the processing flow of FIG. 5B, the case where the classification recipe in other device of the same process as the prepared classification recipe already exists is also considered. For example, in order to improve the yield management efficiency by increasing the number of photographed images in the process in which devices and classification systems are already installed, there is a case where a device is disposed additionally. Description is now made by taking a case where when two devices 1 and 2 are provided as the image photographing devices, the process in which devices are operated is process A, a device installed first is the device 1 and an added device is the device 2 as an example. In this case, since the classification recipe of device 1 and process A exists but the classification recipe of device 2 and process A does not exist, it is efficient that only the classification recipe of device 2 and process A is prepared as compared with preparation of both of the classification recipe of device 1 and process A and the classification recipe of device 2 and process A in the processing flow of FIGS. 5(*b*) and 6. The processing of setting the classification class of device 2 and process A in case where the classification recipe of device 1 and process A exists is described with reference to FIG. 13. Further, the processing flow of preparing the classification recipe is the same as that described in FIG. 5(*b*), although it is not necessary to perform the processing of S513 to S515 of FIG. 5B for the classification recipe existing previously and the processing may be performed only for the classification recipe prepared newly. It is premised that the image of device 2 and process A is stored in the image memory part 213 and the classification recipe of device 1 and process A exists but the classification recipe of device 2 and process A does not exist.

First, the classification recipe for reference is selected (S1301). In the processing S1301, the already existing classification recipe is selected and the following description is made by taking a case where the classification recipe of device 1 and process A is selected as the classification recipe for reference in processing S1301 as an example. Next, the information specifying part 210 reads in the device and process information of the classification recipe (recipe of device 1 and process A) for reference (S1302). The process information may be read in from the classification recipe or may be judged from accompanying information for each image stored in the accompanying information memory part 215 or may be inputted by the user from the input/output part 203.

Next, in processing S1307, the classification recipe (classification recipe of device 2 and process A) of the device (device 2) except the device 1 is newly prepared by the device which photographed the image of the same process A as the classification recipe for reference and the classification class is set. In the processing S1307, first, the device (device 2) except the device 1 is specified by the device which photographed the image of the same process A as the classification recipe for reference (S1303). Then, the classification recipe of device 2 and process A is prepared and the same classification class as the classification class of the classification recipe (classification recipe of device 1 and process A) for reference is defined (S1304). Next, the defect image of the same type as the instruction image registered in the classification class of the classification recipe (classification recipe of device 1 and process A) for reference is specified from among the images of device 2 and process A stored in the image memory part 213 (S1305). The specifying method is as described in description of FIG. 12. The image specified in processing S1305 is registered in the classification class defined in processing S1304 in the classification recipe (classification recipe of device 2 and process A) prepared newly in processing S1303 (S1306).

Figure 13:
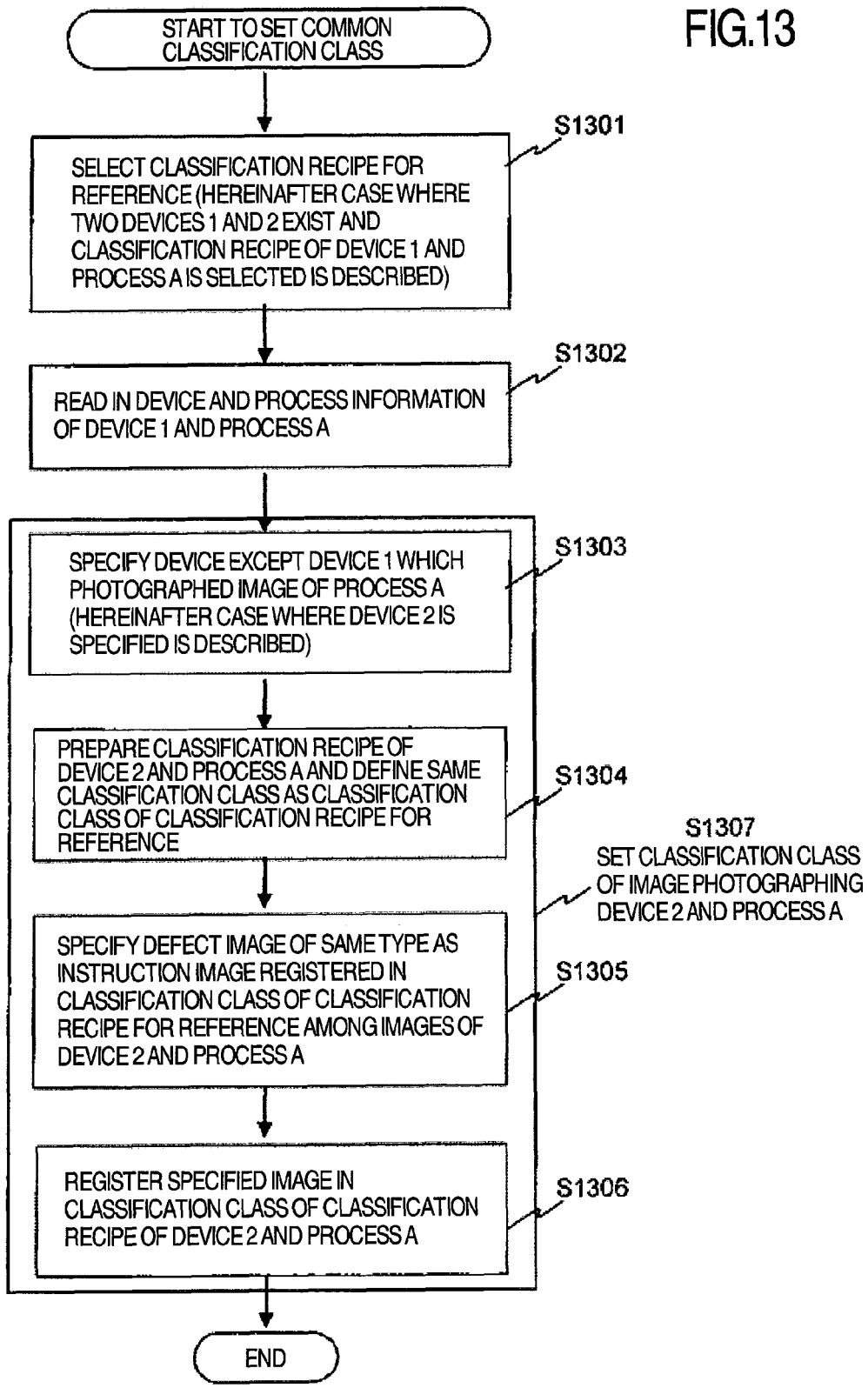
FIG. 13 is a flow chart showing classification class setting processing of a defect classification system of an embodiment 2.

Further, there is also considered a method of performing a conditional branch in which when both of the classification recipe of device 1 and process A and the classification recipe of device 2 and process A do not exist in the classification recipe memory part 214 in case where the classification recipe of process A is specified in processing S601, the processing flow of FIG. 6 is performed and when any of the classification recipe of device 1 and process A and the classification recipe of device 2 and process A exists, the processing flow of FIG. 13 is performed.

As described above, in the embodiment, there has been described the method in which the plural image photographing devices are operated and when the plural classification recipes are present in each combination of the image photographing device and the process, the same classification class as the classification class defined in a classification recipe is defined by another classification recipe in the same process and the defect image of the same type as the image registered in the classification class is specified to be registered, so that the classification definition in the classification recipe is maintained to be the same in the same process. Further, as the method in which the defect image of the same type is specified for the image of different maker and type, there has been described the method in which the images to be compared is converted into the similar images by image conversion and the converted images and the feature amounts of the converted images are subjected to comparison. However, the invention disclosed in this patent specification is not limited to the above embodiments and the modification examples and various modifications can be made. Further, it is needless to say that the above modification examples can be applied to not only the embodiment 1 but also the following other embodiments.

Embodiment 2

Referring now to FIGS. 14 to 18, a second embodiment of the defect classification system according to the present invention is described. The embodiment 2 is the defect classification system which performs recipe preparation in accordance with the same processing flow as the embodiment 1. The embodiment 2 is different from the embodiment 1 in that there are provided, in the defect classification, the function that a new defect is judged as an unknown defect and the function that the unknown defect judged is used to update the classification recipe. The defect classification method and the update method of the classification recipes are now described. The embodiment is described by taking the case where the image photographed by the observation device provided with SEM is classified similarly to the embodiment 1 as an example, although input of the defect classification system according to the embodiment may be any other image except SEM image and may be image photographed using optical means or ion microscope.

Figure 14:
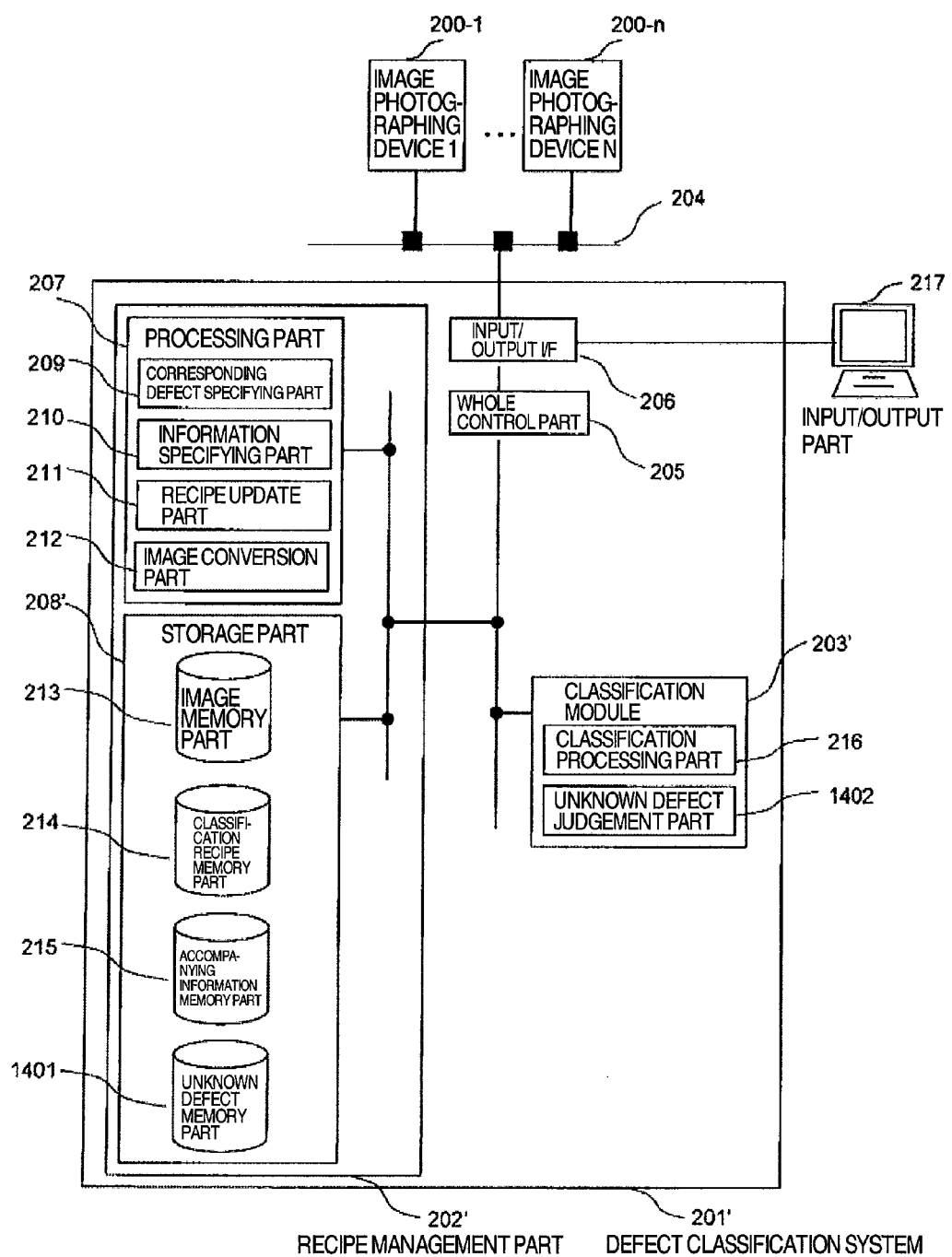
FIG. 14 is a diagram schematically illustrating a configuration example of the defect classification system of the embodiment 2.

FIG. 14 is a schematic diagram illustrating an embodiment of the defect classification system according to the embodiment 2. Description of the same configuration as the defect classification system according to the embodiment 1 is omitted. The defect classification system according to the embodiment 2 is different from the defect classification system according to the embodiment 1 in that an unknown defect judgment part 1402 which judges an unknown defect is provided in the classification module 203' and an unknown defect memory part 1401 which stores therein the judged unknown defect is provided in the storage part 208' of the recipe management part 202'.

Figure 15:
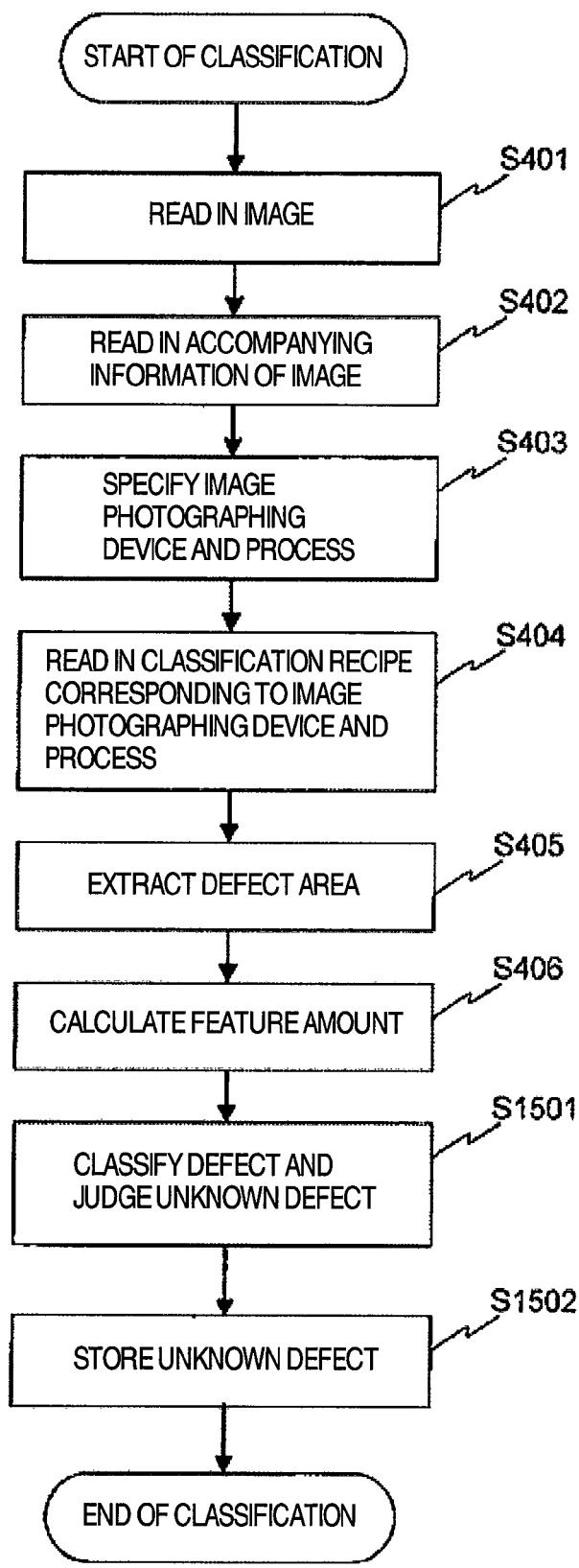
FIG. 15 is a flow chart showing classification processing of the defect classification system of the embodiment 2.

Referring now to FIG. 15, an example of a classification processing flow by the defect classification system according to the embodiment 2 is described. The processing of S401 to S406 in FIG. 15 is the same as the processing flow (FIG. 4) of the classification processing of the embodiment 1 and description thereof is omitted. The embodiment 2 is different from the embodiment 1 in that after the feature amount is calculated (S406), the unknown defect judgment part 1402 subjects defects to classification and unknown defect judgment (S1501) and the judged unknown defect is stored in the unknown defect memory part 1401 (S1502). In the judgment of unknown defect, for example, a method in which judgment is made on the basis of Euclidean distance of the feature point of an object to be classified and the feature amount distribution of the instruction image registered in the classification recipe may be used and for example there is considered a method of judging as an unknown defect when the Euclidean distance is larger than or equal to a set value.

Figure 16:
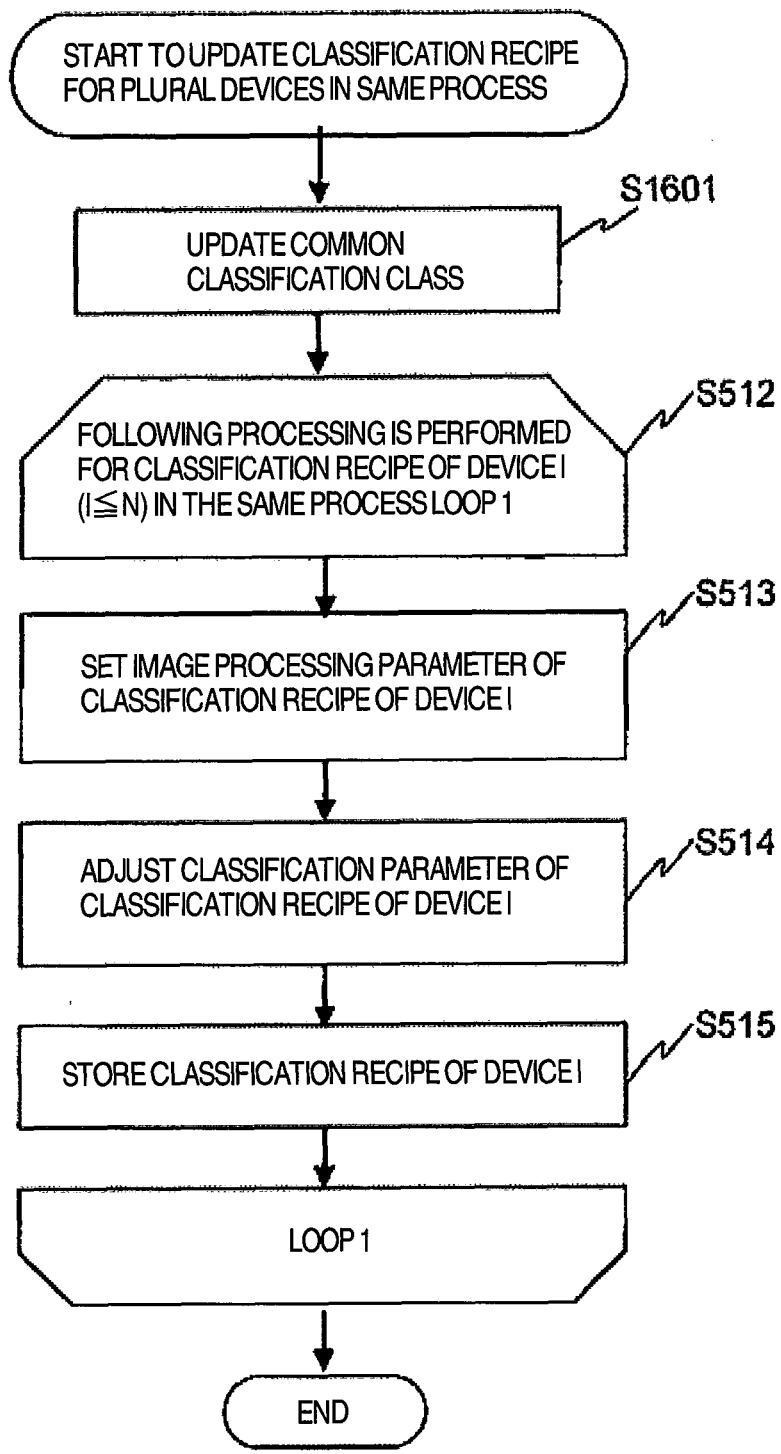
FIG. 16 is a flow chart showing classification recipe update processing of the defect classification system of the embodiment 2.

FIG. 16 is a flow chart showing a processing flow at the time that the same new classification class is defined in the classification recipe corresponding to plural devices of the same process by unknown defect and the classification recipe is updated. The processing of S512 to S515 is the same as the processing described with reference to FIG. 5B of the embodiment 1 and description thereof is omitted. The embodiment is different in that new common classification class is added in processing S1601 and an unknown defect is registered in the new classification class. Detailed description of the processing S1601 is made later with reference to FIG. 17. Further, in the processing of S513 and S514 of FIG. 16, the image processing parameter and the classification parameter before update of the classification recipes may be set as they are without changing them. In this case, the user executes only the processing S1601 and can update plural classification recipes by the same classification definition.

Figure 17:
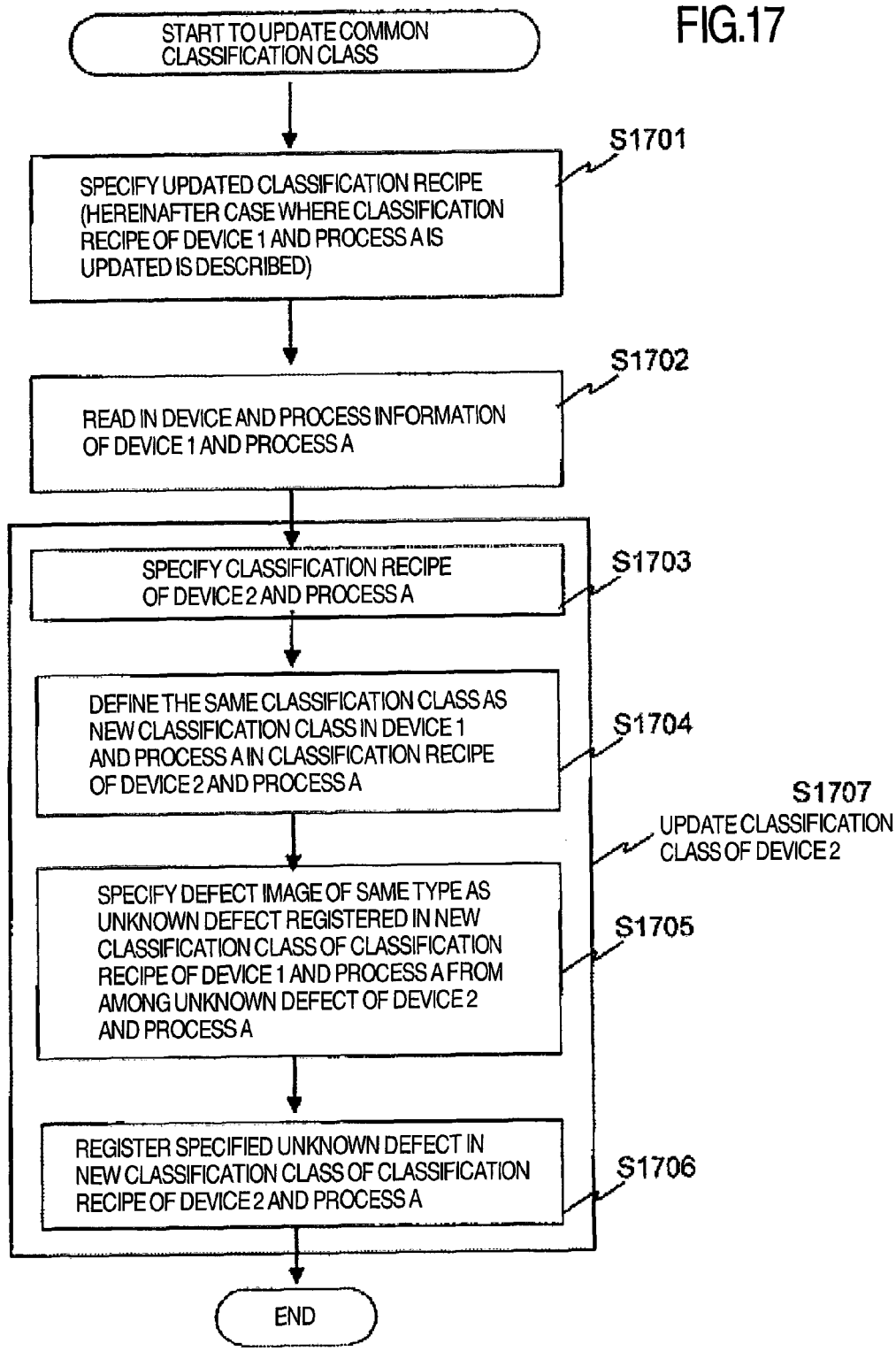
FIG. 17 is a flow chart showing classification class update processing of the defect classification system of the embodiment 2.

Referring to FIG. 17, the update processing flow of the classification recipe is described. The processing flow of FIG. 17 can update the classification recipes in the plural devices in the same process by the same classification definition collectively. In FIG. 17, description is made by taking the case where two devices (devices 1 and 2) are operated in process A as an example. In the example of FIG. 17, it is premised that the classification recipe of device 1 and process A and the classification recipe of device 2 and process A exist and the classification recipe of device 1 and process A is updated.

First, a new class is defined for an unknown defect and the classification recipe having the updated classification class is specified (S1701). As a specifying method, an update flag may be set for each classification recipe when the update processing of the classification recipe described in FIG. 16 is performed and the classification recipe of processing S504 is stored and the classification recipe in which the update flag is set may be specified or GUI described later in FIG. 18 may be used to make selection by the user. Description of FIG. 17 is now made by taking the case where the classification recipe of device 1 and process A is updated and specified in processing S1701 as an example.

Next, in processing S1707, the classification class in the classification recipe in another device for the process specified in processing S1701 is updated. In an example of FIG. 17, the classification class in the classification recipe of device 2 and process A is updated. In processing S1707, first, device and process information of the updated classification recipe is read in from the classification recipe memory part 214 by the information specifying part 210 (S1702) and the same process as the updated classification recipe and the classification recipe of another device are specified (S1703). In processing S1703 of the example of FIG. 17, the classification recipe of device 2 and process A is specified. Next, the same classification class as a new classification class of the classification recipe (in the example of FIG. 17, classification recipe of device 1 and process A) updated before is defined in the classification recipe (in the example of FIG. 17, classification recipe of device 2 and process A) specified in processing S1703 (S 1704). Then, the defect image of the same type as the unknown defect image added before in the new classification class in the classification recipe of device 1 and process A is specified from among unknown defects (that is, unknown defects of device 2 and process A) corresponding to the recipe (in the example of FIG. 17, classification recipe of device 2 and process A) updated in processing S1707 (S1705). The specifying method may use the same method as the method described using FIG. 12 of the embodiment 1. Next, the unknown defect specified in processing S1705 is registered in the new classification class defined in the classification recipe of device 2 and process A in processing S1704 (S1706).

Further, in processing S1705, when the defect image of the same type is specified from among the unknown defects, the number of images to be compared in the processing of specifying the unknown defects of the same type can be reduced by referring to photographing timing of unknown defects stored in the accompanying information memory part 215. In the example of FIG. 17, it can be assumed that the unknown defects of the same type do not occur before the timing that the unknown defects registered in the new classification class of the classification recipe of device 1 and process A were photographed and the defect images of the same type are not contained in the unknown defects photographed before the timing among the unknown defects of device 2 and process A. The defect images of the same type may be specified from among the unknown defects of device 2 and process A having the photographing timing after the timing that the unknown defects registered in the new classification class of device 1 and process A were photographed in the processing flow of FIG. 12.

Figure 18:
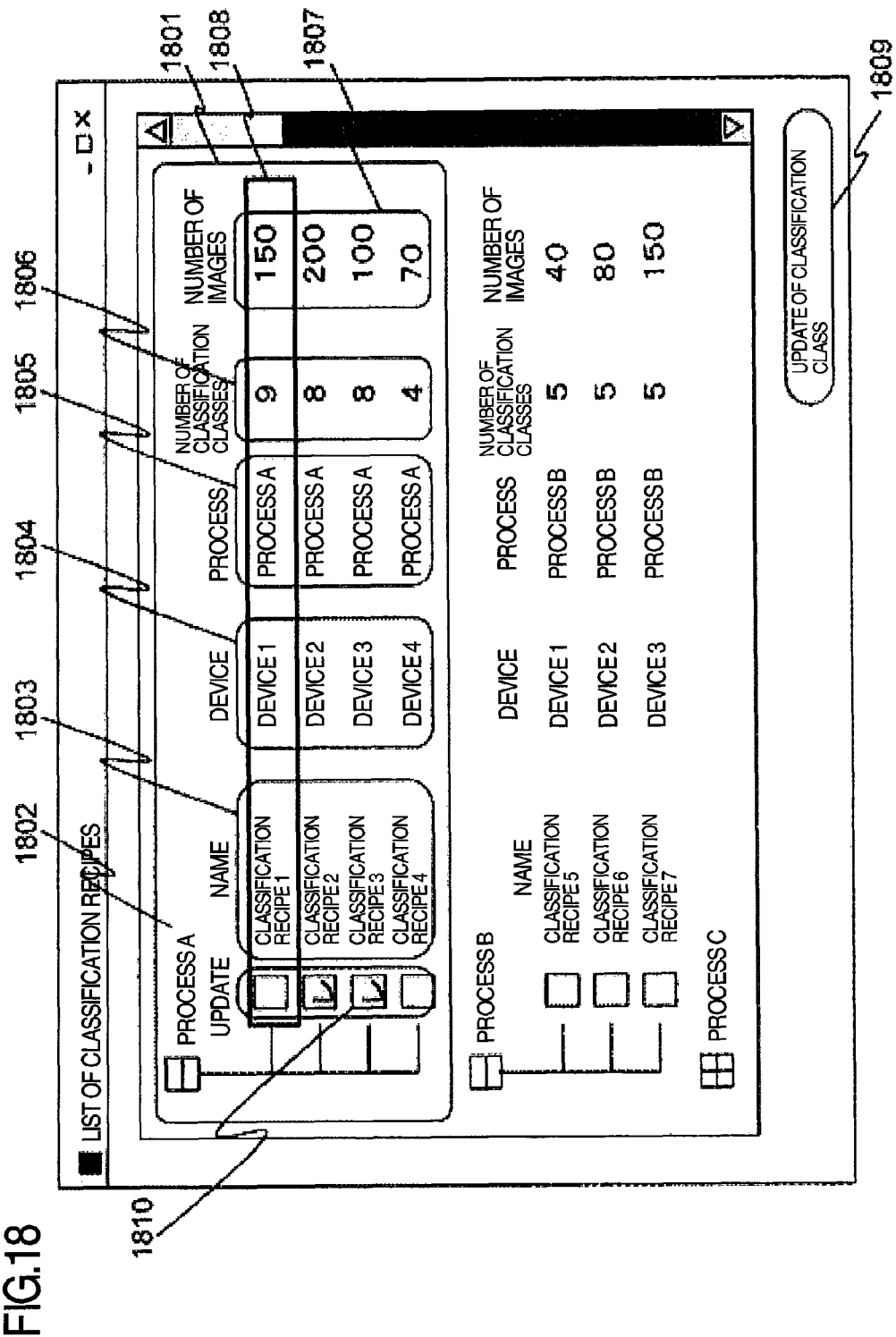
FIG. 18 is a diagram illustrating an example of GUI for selecting classification recipe for a reference in the defect classification system of the embodiment 2.

FIG. 18 shows an example of GUI in which classification recipes of the same process are displayed as a list to update the classification class. 1801 represents an area where the classification recipes of the same process are listed to be displayed. 1802 represents a process name displayed as the list in 1801. In this example of FIG. 18, the classification recipes in the process A of devices 1 to 4 are listed to be displayed. When the classification recipes are listed to be displayed, information containing classification class names (1803), device names (1804), process names (1805), the number of classification classes (1806), the number of images instructed (1807) and the like may be displayed together. A new class is defined in the classification recipes of process A represented by 1801 and an updated classification recipe can be discriminated from the classification recipes which are not updated by means of a method such as enclosed by line as shown by 1808, changing background color and marking. 1809 represents a button for instructing update of the classification recipe of the same process for reference of the classification recipe updated by the processing flow of FIG. 17 and when this button is depressed, the classification recipe of the same process of another device is updated. In this case, there is a possibility that there is a classification list which is not desired to be updated due to the reason that another classification test is performed notwithstanding the classification recipe of the same process. In this case, check boxes (1810) are provided in a corresponding manner to the classification recipes and when the button of 1809 is depressed, the classification class for only the classification recipe having check mark in check box 1810 may be updated.

Embodiment 3

Figure 19:
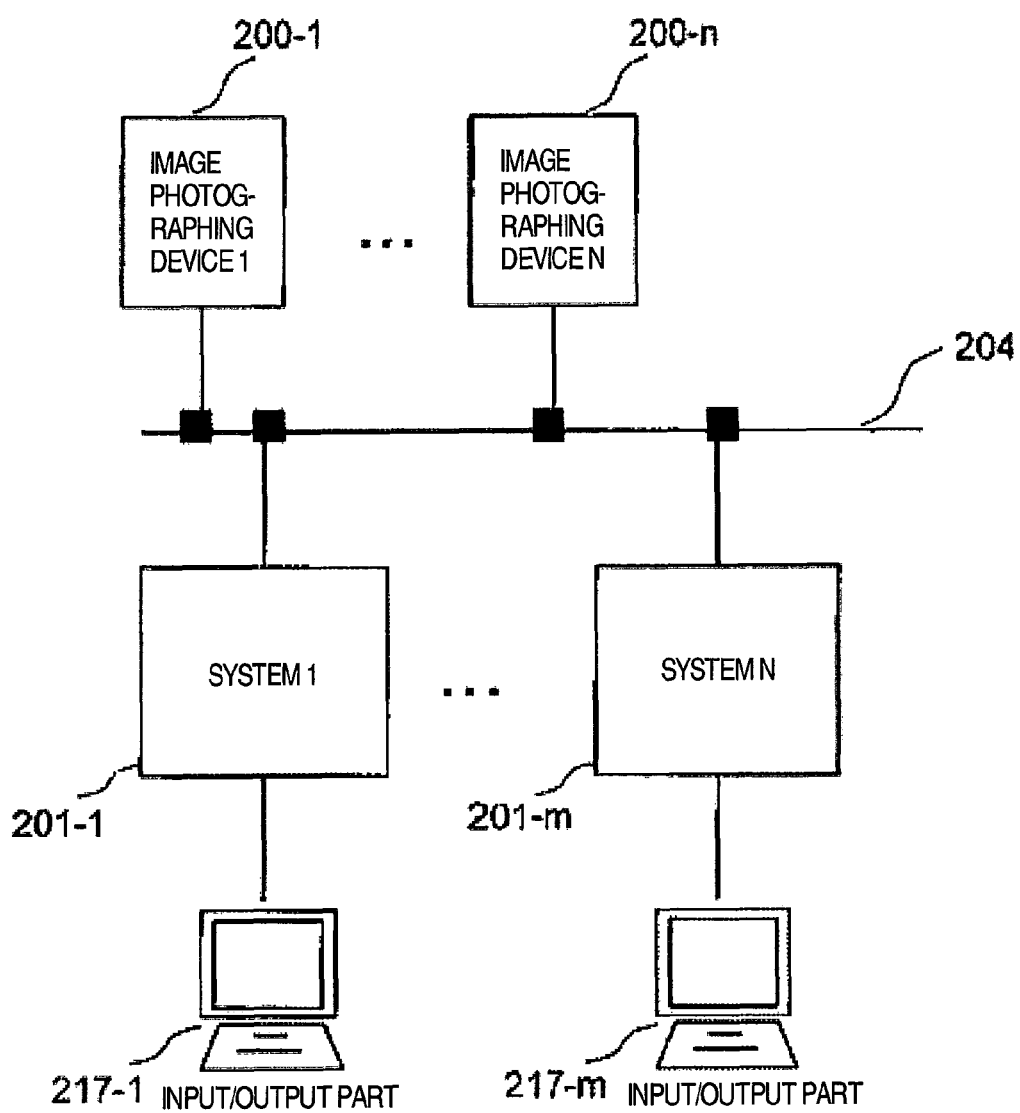
FIG. 19 is a diagram showing processing flow of classification class setting processing of a defect classification system of an embodiment 3.

Referring now to FIGS. 19 and 20, a third embodiment of the defect classification system according to the present invention is described. The embodiment 3 is the defect classification system which performs preparation and update of classification recipes by the same processing flow as the embodiment 2. The embodiment 3 is different from the embodiment 2 in that plural defect classification systems 201 are provided. The preparation method and the update method of the classification recipes in the embodiment 3 are now described. In the embodiment 3, the case where an image photographed by the observation device provided with SEM is classified similarly to the embodiment 2 is described, although input of the defect classification system according to the embodiment may be any input except SEM image and may be an image photographed using optical means or ion microscope.

FIG. 19 is a schematic diagram illustrating an embodiment of the defect classification system according to the embodiment. Description of the same configuration as the defect classification systems according to the embodiments 1 and 2 is omitted. The embodiment is different from the other embodiments in that plural defect classification systems 201 (M≥2) are provided through communication means 204. The defect classification system 201 may be disposed for each image photographing device 200 as M=N or one defect classification system may treat images photographed by plural image photographing devices 200 as M≠N.

Referring to FIG. 20, the processing flow of the classification recipe preparation of the embodiment 3 is described. In description of FIG. 20, the case where when two defect classification systems are installed, the classification recipe of process A is first prepared in the defect classification system 1.

In the processing flow shown in FIG. 20, there are the processing flow (S2001) performed in the defect classification system 1 and the processing flow (S2002) performed in the defect classification system 2 and first the processing flow S2001 is performed.

In the processing flow S2001 of the defect classification system 1, the process of preparing the classification recipe is first designated (S2003). The following description is made to the case where the process A is designated in processing S2003. Next, in the defect image of the process A stored in the defect classification system 1, the classification recipe corresponding to each device is prepared (S2004). In the processing S2004, the processing flow of classification recipe preparation of plural devices in the same process described in FIG. 5B and the processing flow of common classification class setting described in FIG. 6 may be performed. Then, preparation of classification recipe in each device of the process A in the defect classification system 2 is instructed (S2005). A preparation instruction signal of classification recipe, part or all of classification recipes of process A of the defect classification system 1 prepared in processing S2004, information of prepared process and the like are sent to the defect classification system 2.

In processing flow S2002 of the defect classification system 2, the classification recipes in the devices of the process A are prepared on the basis of the classification recipes and process information sent in processing S2005 (S2006). In the processing S2006, since the classification recipes of the process A of the defect classification system 1 are already provided, these classification recipes are used as the classification recipes for the reference in FIG. 13 to perform preparation of classification recipes and setting of classification classes in the processing flow described in FIGS. 5B and 13.

As described above, the case where two defect classification systems are installed has been described, although even when three or more defect classification systems are installed, the embodiment can be applied by instructing the defect classification systems to prepare the classification recipes in processing S2005 and performing the processing flow S2002 in the defect classification systems.

Further, the processing flow of FIG. 20 can be utilized to update the classification recipes in plural defect classification systems. For this purpose, the processing of S2003 and S2004 of FIG. 20 may be replaced by the processing flow described in FIGS. 16 and 17 and the processing S2006 may be also replaced by the processing flow of FIGS. 16 and 17.

As described above, the present invention made by the Inventor has been described concretely on the basis of the embodiments, although it is needless to say that the present invention is not limited to the embodiments and various modifications can be made without departing from the gist of the present invention. The embodiments described above have been described by taking the function of automatically classifying the defect images photographed by the review SEM as an example and the update method of making preparation of the classification recipes having the same classification class and addition of the same classification class which are concrete processing contents has been described, although the present invention can be applied to even other defect observation devices and inspection devices having the classification function and which are necessary to identify the classification class if similar images comparable by image conversion can be produced.

REFERENCE SIGNS LIST 101, 200 . . . image photographing device, 103, 203 . . . classification module, 201 . . . defect classification system, 202 . . . recipe management part, 203 . . . classification module, 204 . . . communication means, 205 . . . whole control part, 206 . . . input/output I/F part, 207 . . . processing part, 208 . . . storage part, 209 . . . corresponding defect specifying part, 210 . . . information specifying part, 211 . . . recipe update part, 212 . . . image conversion part, 213 image memory part, 214 . . . classification recipe memory part, 215 . . . accompanying information memory part, 216 . . . classification processing part, 217 . . . input/output part

The invention claimed is:

1. A defect classification method of classifying defect images using classification recipes corresponding to a device which photographs a sample and a process in which the sample is manufactured, comprising:

a step of defining a same classification class as a classification class defined by a classification recipe of a first image photographing device and by a classification recipe of a second image photographing device corresponding to a same manufacturing process as the classification recipe of the first image photographing device;

a step of specifying a defect image of a same type as an instruction image registered in the classification class defined by the classification recipe of the first image photographing device from among defect images photographed by the second image photographing device; and a step of registering the specified defect image in the same classification class as the classification class of the first image photographing device in which the instruction image is registered, among classification classes defined by the classification recipe of the second image photographing device, wherein the specifying step includes a step of converting the instruction image registered in the classification class defined by the classification recipe of the first image photographing device to resemble an image photographed by the second image photographing device.

2. A defect classification method according to claim 1, wherein the specifying step compares the converted image with the defect image photographed by the second image photographing device to specify the defect image of the same type.

3. A defect classification method according to claim 2, wherein
the specifying step compares a feature amount calculated from the converted image with a feature amount calculated from the defect image photographed by the second image photographing device to specify the defect image of the same type.

4. A defect classification method according to claim 1, wherein
the specifying step includes a step of converting the instruction image registered in the classification class defined by the classification recipe of the first image photographing device and the defect image photographed by the second image photographing device to resemble an image photographed by a third image photographing device.

5. A defect classification method according to claim 4, wherein
the specifying step compares the converted image of the instruction image with a converted image of the defect image to specify the defect image of the same type.

6. A defect classification method according to claim 5, wherein
the specifying step compares a feature amount calculated from the converted image of the instruction image with a feature amount calculated from the converted image of the defect image to specify the defect image of the same type.

7. A defect classification method according to claim 1, wherein
the specifying step specifies the defect image of the same type as the instruction image registered in the classification class defined in the classification recipe of the first image photographing device from among unknown defect images judged as unknown defects among the defect images photographed by the second image photographing device.

8. A defect classification method according to claim 1, comprising
a step of marking the image specified from among the defect images photographed by the second image photographing device.

9. A defect classification method according to claim 1, comprising
a step of displaying the images specified from among the defect images photographed by the second image photographing device in one window of a display picture collectively.

10. A defect classification method according to claim 1, wherein
the registering step registers the converted image in the same classification class as the classification class of the first image photographing device in which the instruction image is registered, among the classification classes defined in the classification recipes of the second image photographing device.

11. A defect classification system connected to a plurality of image photographing devices, comprising:
a first computer including a first processor connected to a first memory and a first input/output interface, the first memory storing instructions that when executed by the first processor causes the first processor to classify defect images photographed by the plural image photographing devices; and
a second computer including a second processor connected to a second memory and a second input/output interface, the second memory storing instructions that when executed by the second processor cause the second processor to:
manage classification recipes in which information for classification is stored;
specify a defect image of a same type as instruction images registered in a classification class of a classification recipe of a first image photographing device of the plurality of image photographing devices from among defect images photographed by a second image photographing device of the plurality of image photographing devices having a same manufacturing process; and
convert the instruction image to resemble the defect image obtained from the second image photographing device.

12. A defect classification system according to claim 11, wherein
the first memory further stores instructions that when executed by the first processor cause the first processor to judge an unknown defect having a classification class which is not defined in a classification recipe, and
wherein the second memory further stores instructions that when executed by the second processor cause the second processor to further specify the defect image of the same type as the instruction image from among defect images judged by the first computer as the unknown defect having the classification class which is not defined in the classification recipe among the defect images photographed by the second image photographing device.

13. A defect classification system according to claim 11, the second memory further stores instructions that when executed by the second processor cause the second processor to output data to a display showing a mark on an image specified from among the defect images photographed by the second image photographing device.

14. A defect classification system according to claim 11, wherein
the second memory further stores instructions that when executed by the second processor cause the second processor to display the images specified from among the images photographed by the second image photographing device in one window of a display.

* * * * *